US009416109B2

United States Patent
Moniz et al.

(10) Patent No.: US 9,416,109 B2
(45) Date of Patent: Aug. 16, 2016

(54) METHODS AND COMPOUNDS USEFUL IN THE SYNTHESIS OF OREXIN-2 RECEPTOR ANTAGONISTS

(71) Applicant: Eisai R&D Management Co., Ltd., Tokyo (JP)

(72) Inventors: George Anthony Moniz, Cambridge, MA (US); Annie Zhu Wilcoxen, North Reading, MA (US); Farid Benayoud, North Andover, MA (US); Jaemoon Lee, Andover, MA (US); Huiming Zhang, Andover, MA (US); Taro Terauchi, Tsukuba (JP); Ayumi Takemura, Tsukuba (JP); Yu Yoshida, Tsukuba (JP); Toshiaki Tanaka, Tsukuba (JP); Keiichi Sorimachi, Tsukuba (JP); Yoshimitsu Naoe, Tsukuba (JP); Yuji Kazuta, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/379,063

(22) PCT Filed: Feb. 14, 2013

(86) PCT No.: PCT/US2013/026204
§ 371 (c)(1),
(2) Date: Aug. 15, 2014

(87) PCT Pub. No.: WO2013/123240
PCT Pub. Date: Aug. 22, 2013

(65) Prior Publication Data
US 2015/0025237 A1    Jan. 22, 2015

Related U.S. Application Data

(60) Provisional application No. 61/600,109, filed on Feb. 17, 2012.

(51) Int. Cl.

| | | |
|---|---|---|
| *C07D 239/34* | (2006.01) | |
| *C07C 69/16* | (2006.01) | |
| *C07C 309/66* | (2006.01) | |
| *C12P 7/22* | (2006.01) | |
| *C07C 309/73* | (2006.01) | |
| *C07D 401/12* | (2006.01) | |
| *C07C 303/28* | (2006.01) | |
| *C07C 29/147* | (2006.01) | |

(52) U.S. Cl.
CPC ............ *C07D 239/34* (2013.01); *C07C 29/147* (2013.01); *C07C 69/16* (2013.01); *C07C 303/28* (2013.01); *C07C 309/66* (2013.01); *C07C 309/73* (2013.01); *C07D 401/12* (2013.01); *C12P 7/22* (2013.01); *C07C 2101/02* (2013.01)

(58) Field of Classification Search
CPC ..... C07D 239/34; C07C 69/16; C07C 309/66; C07C 309/73; C07C 401/12; C07C 303/28; C07C 29/147; C07C 2101/02; C12P 7/22
USPC .......................................................... 549/75
See application file for complete search history.

(56) References Cited

U.S. PATENT DOCUMENTS

| | | | | |
|---|---|---|---|---|
| 5,849,954 | A * | 12/1998 | Carpino et al. | .................... 568/8 |
| 8,268,848 | B2 | 9/2012 | Terauchi et al. | |
| 2012/0095031 | A1* | 4/2012 | Terauchi et al. | .............. 514/269 |

FOREIGN PATENT DOCUMENTS

| | | |
|---|---|---|
| WO | WO 2008/057575 A2 | 5/2008 |
| WO | WO 2008/150364 A1 | 12/2008 |
| WO | WO 2010/032200 A1 | 3/2010 |
| WO | WO 2010/063662 A1 | 6/2010 |

OTHER PUBLICATIONS

Aldrich Chemfiles 2007 7(2), Peptide Synthesis, copyright Sigma Aldrich Co., p. 1-20.*
International Search Report and Written Opinion, PCT/US2013/026204, mailed Apr. 25, 2013.
Valgimigli L et al. The effect of ring nitrogen atoms on the homolytic reactivity of phenolic compounds: understanding the radical-scavenging ability 5-pyrimidinols. Chem Eur J. Oct. 17, 2003; 9(20): 4997-5010.
Yamaguchi K et al. Construction of a cis-cyclopropane via reductive radical decarboxylation. Enantioselective synthesis of cis- and trans-1-arylpiperazyl-2-phenylcyclopropanes designed as antidopaminergic agents. J Org Chem. Jun. 11, 2003; 68(24): 9255-9262.
Response to Office Action, Chinese Patent Application No. 201380009575.3, Oct. 15, 2015.
Response to Office Action, Singapore Patent Application No. 11201403216U, Oct. 27, 2015.
Office Action, Israeli Application No. 232949; Nov. 2, 2015.
Banfi L et al. On the optimization of pig pancreatic lipase catalyzed monoacetylation of prochiral diols. Tetrahedron Asymmetry. 1995; 6(6): 1345-1356.
Oger C et al. Lipase-Catalyzed Regioselective Monoacetylation of Unsymmetrical 1,5-Primary Diols. Journal of Organic Chemistry. 2010; 75: 1892-1897.
Office Action, Singapore Patent Application No. 11201403216U, mailed May 27, 2015.
Office Action, Chinese Patent Application No. 201380009575.3, mailed Jun. 1, 2015.

(Continued)

*Primary Examiner* — Samantha Shterengarts
*Assistant Examiner* — Matt Mauro
(74) *Attorney, Agent, or Firm* — Myers Bigel & Sibley, P.A.

(57) ABSTRACT

The present disclosure provides compounds and methods that are useful for the preparation of compounds useful as orexin-2 receptor antagonists.

32 Claims, No Drawings

(56) References Cited

OTHER PUBLICATIONS

Response to Office Action, Israeli Application No. 232949 (Hebrew) (3 pages), filed Mar. 20, 2016, and English translation thereof (3 pages); Annex A (1 page); Annex B (1 page); Annex C (1 page); Claims (13 pages); specification (69 pages).

Patent Office of the People's Republic of China; Notification to Go Through Formalities of Registration, Notification to Grant Patent Right for Invention, Chinese Patent Application No. 201380009575.3, issued May 24, 2016 (2 pages) and English translation (3 pages).

* cited by examiner

METHODS AND COMPOUNDS USEFUL IN THE SYNTHESIS OF OREXIN-2 RECEPTOR ANTAGONISTS

CROSS REFERENCE TO RELATED APPLICATIONS

This application claims the benefit of U.S. Provisional Patent Application No. 61/600,109, filed Feb. 17, 2012, which is incorporated by reference herein in its entirety.

FIELD OF THE INVENTION

The present invention relates to compounds and methods that are useful for the preparation of compounds useful as orexin-2 receptor antagonists.

BACKGROUND OF THE INVENTION

Orexin receptors are G-protein coupled receptors found predominately in the brain. Their endogenous ligands, orexin-A and orexin-B, are expressed by neurons localized in the hypothalamus. Orexin-A is a 33 amino acid peptide; orexin-B consists of 28 amino acids. (Sakurai T. et al., Cell, 1998, 92, 573-585). There are two subtypes of orexin receptors, $OX_1$ and $OX_2$; $OX_1$ binds orexin-A preferentially, while $OX_2$ binds both orexin-A and -B. Orexins stimulate food consumption in rats, and it has been suggested that orexin signaling could play a role in a central feedback mechanism for regulating feeding behavior (Sakurai et al., supra). It has also been observed that orexins control wake-sleep conditions (Chemelli R. M. et al., Cell, 1999, 98, 437-451). Orexins may also play roles in brain changes associated with opioid and nicotine dependence (S. L. Borgland et al., Neuron, 2006, 49, 598-601; C. J. Winrow et al., Neuropharmacology, 2010, 58, 185-194), and ethanol dependence (J. R. Shoblock et al., Psychopharmacology, 2011, 215, 191-203). Orexins have additionally been suggested to play a role in some stress reactions (T. Ida et al., Biochem. Biophys. Res. Commun., 2000, 270, 318-323).

Compounds such as (1R,2S)-2-(((2,4-dimethylpyrimidin-5-yl)oxy)methyl)-2-(3-fluorophenyl)-N-(5-fluoropyridin-2-yl)cyclopropanecarboxamide (Compound A, below) have been found to be potent orexin receptor antagonists, and may be useful in the treatment of sleep disorders such as insomnia, as well as for other therapeutic uses.

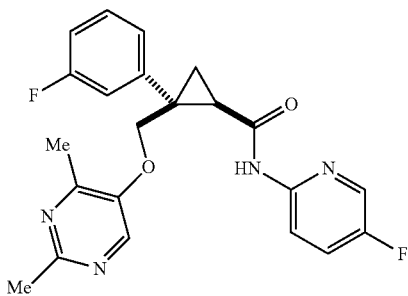

Compound A

There is thus a need for synthetic methods and intermediates useful in the preparation of Compound A and related compounds. It is, therefore, an object of the present application to provide such synthetic methods and intermediates.

SUMMARY

Provided herein are compounds and methods that are useful for the preparation of compounds useful as orexin-2 receptor antagonists.

Provided is a process for making a compound of Formula I,

I wherein Ar is an aryl such as phenyl, which aryl may be unsubstituted, or substituted 1-3 times, for example, with substituents independently selected from the group consisting of: halo, $C_{1-6}$alkyl, $C_{1-6}$alkoxy, and halo$C_{1-6}$alkyl, the method comprising one or more of the steps of:

i) providing a composition comprising a compound of Formula II:

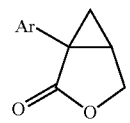

II wherein Ar is as given above, and an organic solvent, wherein said composition is at a temperature of from −30 to 40° C., or from −30 to 30° C., or from −30 to 10° C., or from −10 to 0° C., or from −10 to −5° C.; and ii) adding to said composition a hydride reducing agent, wherein said agent reduces said compound of Formula II into said compound of Formula I, to thereby make said compound of Formula I.

In some embodiments, Ar is phenyl, which phenyl may be unsubstituted, or substituted 1-3 times with a halo independently selected from the group consisting of: chloro, fluoro, bromo, and iodo.

In some embodiments, the organic solvent is an aromatic hydrocarbon solvent, an aliphatic hydrocarbon solvent, a halogenated hydrocarbon solvent or an ether solvent.

In some embodiments, the process may further include the step of mixing (e.g., by stirring) the composition after said adding step for a time of 12 to 24 hours.

In some embodiments, the process may further include the step of quenching the reduction by adding to said composition a mild aqueous acid (e.g., citric acid, EDTA or tartaric acid).

In some embodiments, the compound of Formula II has the absolute stereochemistry of Formula IIa:

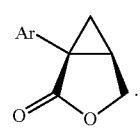

IIa

In some embodiments, the compound of Formula II has an enantiomeric excess (ee) of the Formula IIa stereoisomer of at least 75, 80, 85, 90, 95, 98, 99%, or greater.

In some embodiments, the compound of Formula II or Formula IIa is the compound:

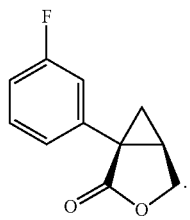 [SMILES: O=C1OC[C@@H]2C[C@]12c1cccc(F)c1]

In some embodiments, the compound of Formula I has the absolute stereochemistry of Formula Ia:

In some embodiments, the compound of Formula I has an enantiomeric excess (ee) of the Formula Ia stereoisomer of at least 75, 80, 85, 90, 95, 98, 99%, or greater.

In some embodiments, the compound of Formula I or Formula Ia is:

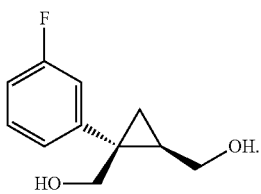 [SMILES: OC[C@@H]1C[C@@]1(CO)c1cccc(F)c1]

Also provided is compound of Formula III:

wherein Ar is an aryl such as phenyl, which aryl may be unsubstituted, or substituted 1-3 times, for example with substituents independently chosen from the group consisting of: halo, $C_{1-6}$alkyl, $C_{1-6}$alkoxy, and halo$C_{1-6}$alkyl.

In some embodiments, Ar is phenyl, which phenyl may be unsubstituted, or substituted 1-3 times with a halo independently selected from the group consisting of: chloro, fluoro, bromo, and iodo.

In some embodiments, the compound is:

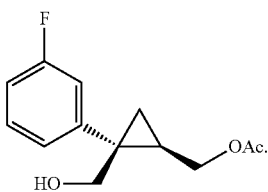 [SMILES: CC(=O)OC[C@@H]1C[C@@]1(CO)c1cccc(F)c1]

Also provided is a process for making a compound of Formula III:

wherein Ar is aryl such as phenyl, which aryl may be unsubstituted, or substituted 1-3 times, for example with substituents independently selected from the group consisting of: halo, $C_{1-6}$alkyl, $C_{1-6}$alkoxy, and halo$C_{1-6}$alkyl, comprising reacting a mixture of:

i) a compound of Formula Ia:

wherein Ar is as given above,
ii) vinyl acetate,
iii) a lipase, and
iv) an organic solvent
for a time of from 5 to 36 hours, or from 7 to 18 hours, to thereby make the compound of Formula III.

In some embodiments, Ar is phenyl, which phenyl may be unsubstituted, or substituted 1-3 times with a halo independently selected from the group consisting of: chloro, fluoro, bromo, and iodo.

In some embodiments, the organic solvent is tetrahydrofuran, 2-methyltetrahydrofuran, an ether solvent, acetone, or acetonitrile.

In some embodiments, the lipase is a *Candida Antarctica* lipase, for example, a *Candida Antarctica* B lipase, which may be coupled to solid support such as an acrylic resin.

In some embodiments, the process may further include the step of filtering the mixture after said reacting to produce a filtrate, and may further include concentrating the filtrate to produce a concentrated filtrate. In some embodiments, the process may further include the step of washing the concentrated filtrate with water or water comprising a salt (e.g., a solution of 15-20% NaCl in water).

Also provided is a compound of Formula IV:

wherein:
Ar is an aryl such as phenyl, which aryl may be unsubstituted, or substituted 1-3 times, for example with substituents independently selected from the group consisting of: halo, $C_{1-6}$alkyl, $C_{1-6}$alkoxy, and halo$C_{1-6}$alkyl; and
$R_1$ is a leaving group.

In some embodiments, Ar is phenyl, which phenyl may be unsubstituted, or substituted 1-3 times with a halo independently selected from the group consisting of: chloro, fluoro, bromo, and iodo.

In some embodiments, the leaving group is a sulfonate ester leaving group selected from the group consisting of: mesylate, tosylate, nosylate, benzene sulfonate, and brosylate.

In some embodiments, the compound is:

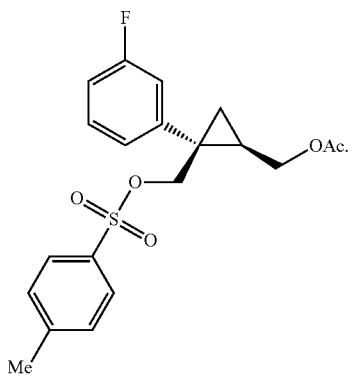 [SMILES: CC(=O)OC[C@@H]1C[C@@]1(COS(=O)(=O)c1ccc(C)cc1)c1cccc(F)c1]

In some embodiments, the compound of Formula IV has the absolute stereochemistry of Formula IVa:

IVa

In some embodiments, the compound of Formula IV has an enantiomeric excess (ee) of the Formula IVa stereoisomer of at least 75, 80, 85, 90, 95, 98, 99%, or greater.

Further provided is a process for making a compound of Formula IV:

IV wherein Ar is an aryl such as phenyl, which aryl may be unsubstituted, or substituted 1-3 times, for example with substituents independently selected from the group consisting of: halo, $C_{1-6}$alkyl, $C_{1-6}$alkoxy, and halo$C_{1-6}$alkyl; and
$R_1$ is a sulfonate ester leaving group,
said process comprising reacting a compound of Formula III:

III wherein Ar is as given above,
with a compound selected from the group consisting of: tosyl chloride, mesyl chloride, nosyl chloride, toluenesulfonyl chloride, toluenesulfonic anhydride and methanesulfonic anhydride, wherein said reacting is carried out in an organic solvent in the presence of a base,
to thereby make said compound of Formula IV.

In some embodiments, Ar is phenyl, which phenyl may be unsubstituted, or substituted 1-3 times with a halo independently selected from the group consisting of: chloro, fluoro, bromo, and iodo.

In some embodiments, the reacting is carried out for a time of from 10 minutes to 2 hours.

In some embodiments, the base is an organic amine or potassium carbonate.

In some embodiments, the compound of Formula III is:

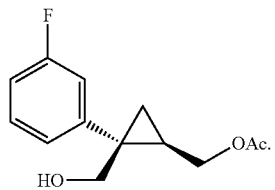

In some embodiments, the compound of Formula IV has the absolute stereochemistry of Formula IVa:

IVa

In some embodiments, the compound of Formula IV has an enantiomeric excess (ee) of the Formula IVa stereoisomer of at least 75, 80, 85, 90, 95, 98, 99%, or greater.

Also provided is a process for making a compound of Formula V,

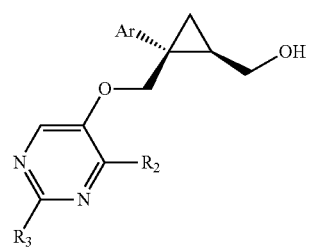

V wherein Ar is an aryl such as phenyl, which aryl may be unsubstituted, or substituted 1-3 times, for example with substituents independently selected from the group consisting of: halo, $C_{1-6}$alkyl, $C_{1-6}$alkoxy, and halo$C_{1-6}$alkyl; and
$R_2$ and $R_3$ are each independently selected from the group consisting of: hydrogen, $C_{1-6}$alkyl, halo$C_{1-6}$ alkyl, $C_{1-6}$alkoxy, and hydroxy$C_{1-6}$alkyl,
comprising the steps of:
a) stirring a mixture of:
i) a compound of Formula IV:

IV wherein Ar is as given above; and
$R_1$ is a leaving group,
ii) a substituted pyrimidine of Formula VI:

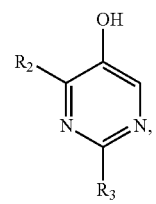

VI wherein $R_2$ and $R_3$ are as given above;
iii) a base; and
iv) an organic solvent,
at a temperature of from 65-70° C., for 1 to 12 hours; and then
b) reacting the mixture with an aqueous base for a time of from 2 to 20 hours,
to thereby make said compound of Formula V.

In some embodiments, Ar is phenyl, which phenyl may be unsubstituted, or substituted 1-3 times with a halo independently selected from the group consisting of: chloro, fluoro, bromo, and iodo.

In some embodiments, $R_2$ and $R_3$ are each independently selected from the group consisting of: hydrogen and $C_{1-6}$alkyl.

In some embodiments, the compound of Formula IV has the absolute stereochemistry of Formula IVa:

IVa

In some embodiments, the compound of Formula IV has an enantiomeric excess (ee) of the Formula IVa stereoisomer of at least 75, 80, 85, 90, 95, 98, 99%, or greater.

Further provided is a process for making a compound of Formula VI:

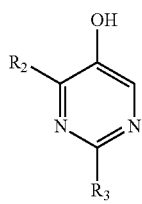

VI wherein $R_2$ and $R_3$ are each independently selected from the group consisting of: hydrogen and $C_{1-6}$ alkyl, comprising the step of heating a mixture of:
i) a compound of Formula B:

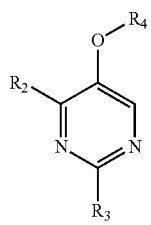

B wherein:
$R_2$ and $R_3$ are as given above; and
$R_4$ is $C_{1-6}$ alkyl,
ii) an alkoxide or hydroxide salt,
iii) a thiol, and
iv) an organic solvent,
to thereby make said compound of Formula VI.

In some embodiments, the heating is to a temperature of from 50° C. to 140° C. In some embodiments, heating comprises boiling or refluxing the mixture.

In some embodiments, the heating is carried out in a time of from 5 to 50 hours.

Also provided is a process for making a compound of Formula B:

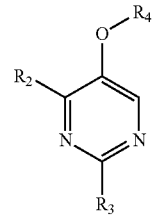

B wherein:
$R_2$ and $R_3$ are each independently selected from the group consisting of: hydrogen and $C_{1-6}$ alkyl; and
$R_4$ is $C_{1-6}$ alkyl,
comprising mixing:
i) a compound of Formula A:

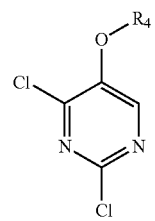

A wherein $R_4$ is as given above,
ii) trimethylaluminum,
iii) a palladium catalyst, and
iv) an organic solvent,
to thereby make said compound of Formula B.

In some embodiments, the mixing step is carried out for a time of from 12 to 48 hours.

In some embodiments, the mixing step is carried out at a temperature of from 20° C. to 110° C.

In some embodiments, the process further includes a step of quenching the reaction, e.g., with water comprising a base (e.g., a hydroxide such as sodium hydroxide).

In some embodiments, the process further includes a step of treating said compound of Formula B with a solution comprising hydrogen chloride and a solvent such as an alcohol (e.g., isopropyl alcohol) to obtain said compound of Formula B as a hydrochloride salt. In some embodiments this is done after a quenching step.

Further provided is a process for making a compound of Formula B:

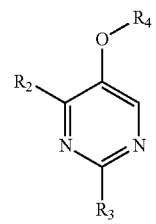

B wherein:
$R_2$ and $R_3$ are each independently selected from the group consisting of: hydrogen and $C_{1-6}$ alkyl; and
$R_4$ is $C_{1-6}$ alkyl, comprising mixing:
i) a compound of Formula A:

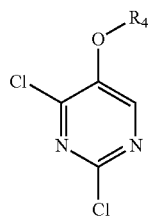

wherein $R_4$ is as given above, ii) a nickel catalyst (e.g., Ni(acac)$_2$, Ni(PPh$_3$)$_2$Cl$_2$, or Ni(dppp)Cl$_2$), iii) an alkylmagnesium halide, and iv) an organic solvent, to thereby make said compound of Formula B.

In some embodiments, the mixing is carried out for a time of from 6 to 36 hours.

In some embodiments, the mixing is carried out at a temperature of from 10° C. to 30° C.

In some embodiments, the process further includes a step of quenching the reaction, e.g., with water comprising an acid (e.g., citric acid). In some embodiments, the process further includes a step of adding ammonium hydroxide after the quenching step.

In some embodiments, the process further includes reacting the compound of Formula B with a solution comprising hydrogen chloride and a solvent such as an alcohol (e.g., isopropyl alcohol) to obtain the compound of Formula B as a hydrochloride salt.

Also provided is a process for making a compound of Formula VII:

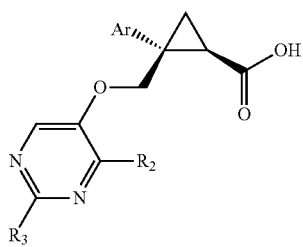

wherein Ar is an aryl such as phenyl, which aryl may be unsubstituted, or substituted 1-3 times, for example with substituents independently selected from the group consisting of: halo, $C_{1-6}$ alkyl, $C_{1-6}$ alkoxy, and halo$C_{1-6}$ alkyl; and $R_2$ and $R_3$ are each independently selected from the group consisting of: hydrogen, $C_{1-6}$ alkyl, halo$C_{1-6}$ alkyl, $C_{1-6}$ alkoxy, and hydroxy$C_{1-6}$ alkyl, comprising the steps of:
a) oxidizing a compound of Formula V:

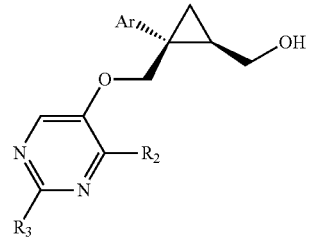

wherein Ar, $R_2$ and $R_3$ are as given above, with a first oxidizing agent, to form an aldehyde of Formula VIII:

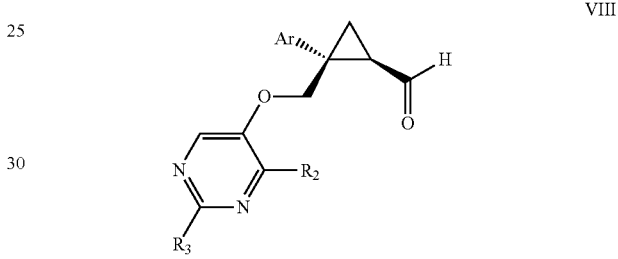

wherein Ar, $R_2$ and $R_3$ are as given above; and then b) oxidizing the aldehyde of Formula VIII with a second oxidizing agent, to thereby make said compound of Formula VII.

In some embodiments, Ar is phenyl, which phenyl may be unsubstituted, or substituted 1-3 times with a halo independently selected from the group consisting of: chloro, fluoro, bromo, and iodo.

In some embodiments, $R_2$ and $R_3$ are each independently selected from the group consisting of: hydrogen and $C_{1-6}$alkyl.

In some embodiments, the first oxidizing agent is sodium hypochlorite.

In some embodiments, oxidizing of step a) is catalyzed with an effective amount of 2,2,6,6-tetramethylpiperidine 1-oxyl (TEMPO).

In some embodiments, the second oxidizing agent is sodium chlorite.

In some embodiments, the first oxidizing agent and the second oxidizing agent are the same. In some embodiments, the first oxidizing agent and the second oxidizing agent are different.

In some embodiments, the oxidizing of step a) and/or step b) is carried out in an organic solvent (e.g., dichloromethane, tetrahydrofuran, 2-methyltetrahydrofuran, toluene, acetonitrile, or ethyl acetate).

Further provided is a process for preparing a compound of Formula VII:

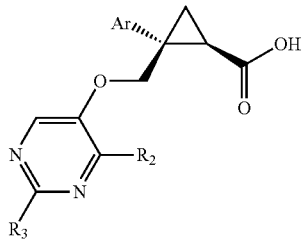

wherein Ar is an aryl such as phenyl, which aryl may be unsubstituted, or substituted 1-3 times, for example with substituents independently selected from the group consisting of: halo, $C_{1-6}$alkyl, $C_{1-6}$alkoxy, and halo$C_{1-6}$alkyl; and $R_2$ and $R_3$ are each independently selected from the group consisting of: hydrogen, $C_{1-6}$alkyl, halo$C_{1-6}$ alkyl, $C_{1-6}$alkoxy, and hydroxy$C_{1-6}$alkyl, comprising: oxidizing a compound of Formula V:

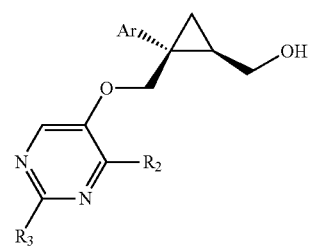

wherein Ar, $R_2$ and $R_3$ are as given above,
with sodium hypochlorite and sodium chlorite,
to thereby make said compound of Formula VII.

In some embodiments, Ar is phenyl, which phenyl may be unsubstituted, or substituted 1-3 times with a halo independently selected from the group consisting of: chloro, fluoro, bromo, and iodo.

In some embodiments, $R_2$ and $R_3$ are each independently selected from the group consisting of: hydrogen and $C_{1-6}$alkyl.

In some embodiments, the oxidizing with sodium hypochlorite and sodium chlorite is carried out simultaneously.

In some embodiments, the oxidizing is catalyzed with an effective amount of 2,2,6,6-tetramethylpiperidine 1-oxyl (TEMPO).

Also provided is a process for making a compound of Formula IX:

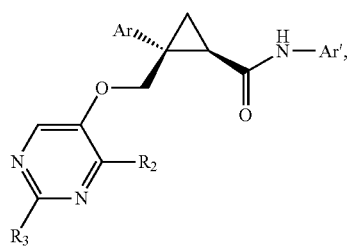

wherein:
Ar is an aryl such as phenyl, which aryl may be unsubstituted, or substituted 1-3 times, for example with substituents independently selected from the group consisting of: halo, $C_{1-6}$alkyl, $C_{1-6}$alkoxy, and halo$C_{1-6}$alkyl;

$R_2$ and $R_3$ are each independently selected from the group consisting of: hydrogen, $C_{1-6}$alkyl, halo$C_{1-6}$ alkyl, $C_{1-6}$alkoxy, and hydroxy$C_{1-6}$alkyl; and Ar' is a pyridine group:

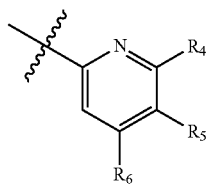

wherein:
$R_4$ is selected from the group consisting of: hydrogen, halo, $C_{1-6}$alkyl, $C_{1-6}$alkoxy, and ($C_{1-6}$alkoxy)$C_{1-6}$alkyl;
$R_5$ is selected from the group consisting of: hydrogen, halo, $C_{1-6}$alkyl, and halo$C_{1-6}$alkyl; and
$R_6$ is selected from the group consisting of: hydrogen, halo, $C_{1-6}$alkyl, halo$C_{1-6}$alkyl, $C_{1-6}$alkoxy, ($C_{1-6}$alkoxy)$C_{1-6}$alkyl, and cyano;

comprising the step of reacting a compound of Formula VII:

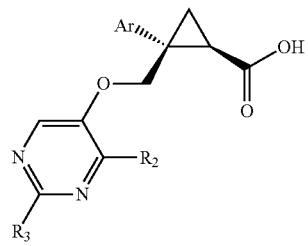

wherein Ar, $R_2$ and $R_3$ are as given above,
with a compound of Formula X:

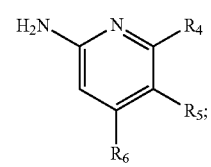

wherein $R_4$, $R_5$, and $R_6$ are as given above,
said reacting carried out in an organic solvent in the presence of an organic amine and an amide coupling agent,
to thereby make said compound of Formula IX.

In some embodiments, Ar is phenyl, which phenyl may be unsubstituted, or substituted 1-3 times with a halo independently selected from the group consisting of: chloro, fluoro, bromo, and iodo.

In some embodiments, $R_2$ and $R_3$ are each independently selected from the group consisting of: hydrogen and $C_{1-6}$alkyl.

DETAILED DESCRIPTION

All U.S. Patent references are hereby incorporated by reference herein to the extent they are consistent with the present descriptions.

A. DEFINITIONS

Compounds of this invention include those described generally above, and are further illustrated by the embodiments, sub-embodiments, and species disclosed herein. As used herein, the following definitions shall apply unless otherwise indicated.

As described herein, compounds of the invention may optionally be substituted with one or more substituents, such as are illustrated generally above, or as exemplified by particular classes, subclasses, and species of the invention. In general, the term "substituted" refers to the replacement of hydrogen in a given structure with a specified substituent. Unless otherwise indicated, a substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

"Isomers" refer to compounds having the same number and kind of atoms and hence the same molecular weight, but differing with respect to the arrangement or configuration of the atoms.

"Stereoisomers" refer to isomers that differ only in the arrangement of the atoms in space.

"Absolute stereochemistry" refers to the specific spatial arrangement of atoms or groups in a chemical compound about an asymmetric atom. For example, a carbon atom is asymmetric if it is attached to four different types of atoms or groups of atoms.

"Diastereoisomers" refer to stereoisomers that are not mirror images of each other.

"Enantiomers" refers to stereoisomers that are non-superimposable mirror images of one another.

Enantiomers include "enantiomerically pure" isomers that comprise substantially a single enantiomer, for example, greater than or equal to 90%, 92%, 95%, 98%, or 99%, or equal to 100% of a single enantiomer.

"Enantiomerically pure" as used herein means a compound, or composition of a compound, that comprises substantially a single enantiomer, for example, greater than or equal to 90%, 92%, 95%, 98%, or 99%, or equal to 100% of a single enantiomer.

"Stereomerically pure" as used herein means a compound or composition thereof that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of diastereomers, and substantially free of the enantiomer, of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. See, e.g., U.S. Pat. No. 7,189,715.

"R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry. Section E, Stereochemistry.

"Enantiomeric excess" (ee) of an enantiomer, when expressed as a percentage, is [(the mole fraction of the major enantiomer) minus (the mole fraction of the minor enantiomer)]×100.

"Stable" as used herein refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

"Refluxing" as used herein refers to a technique in which vapors from a boiling liquid are condensed and returned to the mixture from which it came, typically by boiling the liquid in a vessel attached to a condenser.

"Concentrating" as used herein refers to reducing the volume of solvent in a composition or mixture.

A "filtrate" is the liquid produced after filtering thereof; filtering typically includes the removal of a suspension of solid from the liquid.

An "organic" compound as used herein is a compound that contains carbon. Similarly, an "organic solvent" is a compound containing carbon that is useful as a solvent. Examples of organic solvents include, but are not limited to, acid amides such as N,N-dimethylformamide and N,N-dimethylacetamide; alcohols such as ethanol, methanol, isopropanol, amyl alcohol, ethylene glycol, propylene glycol, 1-butanol, butyl carbitol acetate and glycerin; aliphatic hydrocarbons such as hexane and octane; aromatic hydrocarbons such as toluene, xylenes and benzene; ketones such as acetone, methyl ethyl ketone and cyclohexanone; halogenated hydrocarbons such as methylene chloride, chlorobenzene and chloroform; esters such as ethyl acetate, amyl acetate and butyl acetate; ethers such as tetrahydrofuran, 2-methyltetrahydrofuran, 1,4-dioxane, tert-butyl methyl ether, diethyl ether and ethylene glycol dimethyl ether; nitriles such as acetonitrile; and sulfoxides such as dimethylsulfoxide.

An "inorganic" compound is a compound not containing carbon.

A "hydrocarbon" is an organic compound consisting of carbon and hydrogen atoms. Examples of hydrocarbons useful as "hydrocarbon solvents" include, but are not limited to, an "aromatic hydrocarbon solvent" such as benzene, toluene, xylenes, etc., and an "aliphatic hydrocarbon solvent" such as pentane, hexane, heptane, etc.

An "amine", "organic amine", "amine base" or "organic amine base" as used herein refers to an organic compound having a basic nitrogen atom (R—NR'R"), and may be a primary (R—NH$_2$), secondary (R—NHR') or tertiary (R—NR'R") amine. R, R' and R" may be independently selected from the group consisting of alkyl (e.g., cycloalkyl), aryl and heteroaryl, which groups may be optionally substituted, or R and R', R and R" and/or R' and R", when present, may also combine to form cyclic or heteroalicyclic ring. The term heteroalicyclic as used herein refers to mono-, bi- or tricyclic ring or ring systems having one or more heteroatoms (for example, oxygen, nitrogen or sulfur) in at least one of the rings. The ring system may be a "saturated ring", which means that the ring does not contain any alkene or alkyne moieties, or it may also be an "unsaturated ring" which means that it contains at least one alkene or alkyne moiety provided that the ring system is not aromatic. The cyclic or heteroalicyclic group may be unsubstituted or substituted as defined herein.

In some embodiments the amine is aromatic. Examples of aromatic amines include, but are not limited to, pyridine, pyrimidine, quinoline, isoquinolines, purine, pyrrole, imidazole, and indole. The aromatic amines may be substituted or unsubstituted.

The term "optionally substituted" is used interchangeably with the phrase "substituted or unsubstituted" and means that a group may be substituted by one or more suitable substituents which may be the same or different. In some embodiments, suitable substituents may be selected from alkyl, cycloalkyl, biaryl, carbocyclic aryl, heteroalicyclic, heteroaryl, acyl, amidino, amido, amino, alkoxyamino, carbamoyl, carboxy, cyano, ether, guanidine, hydroxamoyl, hydroxyl, imino, isocyanato, isothiocyanato, halo, nitro, silyl, sulfonyl, sulfinyl, sulfenyl, sulfonato, sulfamoyl, sulfonamido, thiocarbonyl, thiol, thiocyanato, thiocarbamoyl, thioamido and urea.

Examples include, but are not limited to, triethylamine, pyridine, dimethylaminopyridine, N-methylmorpholine, Hunig's base (N,N-diisopropylethylamine), and 1,8-diazabicyclo[5.4.0]undec-7-ene (DBU).

An "amide" as used herein refers to an organic functional group having a carbonyl group (C=O) linked to a nitrogen atom (N).

An "amide coupling agent" is an agent that may be used to couple a nitrogen and carboxyl group to form an amide, typically by activating the carboxyl group. Examples of amide coupling agents include, but are not limited to, carbodiimides such as N,N'-dicyclohexylcarbodiimide (DCC), N-(3-dimethylaminopropyl)-N'-ethylcarbodiimide (EDC) or N-(3-dimethylaminopropyl)-N'-ethylcarbodiimide hydrochloride (EDAC), N,N'-diisopropylcarbodiimide (DIC); imidazoliums such as 1,1'-carbonyldiimidazole (CDI), 1,1'-carbonyl-di-(1,2,4-triazole) (CDT); uronium or guanidinium salts such as O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), and O-(benzotriazol-1-yl)-N,N,N',N'-tetramethyluronium tetrafluoroborate (TBTU); phosphonium salts such as benzotriazol-1-yloxy)tris(dimethylamino)phosphonium hexafluorophosphate (BOP or Castro's reagent), (benzotriazol-1-yloxy)tripyrrolidinophosphonium hexafluorophosphate (PyBOP®, Merck KGaA, Germany), 7-azabenxotriazol-1-yloxy)tripyrrolidinophosphonium hexafluorophosphate (PyAOP); alkyl phosphonic acid anhydrides such as ®T3P (Archimica, Germany), etc.

"Aqueous" is a solution in which water is the dissolving medium, or solvent. An "aqueous base" is a base in water. An "aqueous acid" is an acid in water.

An "acid" is a compound that can act as a proton donor or electron pair acceptor, and thus can react with a base. The strength of an acid corresponds to its ability or tendency to lose a proton. A "strong acid" is one that completely dissociates in water. Examples of strong acids include, but are not limited to, hydrochloric acid (HCl), hydroiodic acid (HI), hydrobromic acid (HBr), perchloric acid (HClO$_4$), nitric acid (HNO$_3$), sulfuric acid (H$_2$SO$_4$), etc. A "weak" or "mild" acid, by contrast, only partially dissociates, with both the acid and the conjugate base in solution at equilibrium. Examples of mild acids include, but are not limited to, carboxylic acids such as acetic acid, citric acid, formic acid, gluconic acid, lactic acid, oxalic acid, tartaric acid, ethylenediaminetetraacetic acid (EDTA), etc.

A "base" is a compound that can accept a proton (hydrogen ion) or donate an electron pair. A base may be organic (e.g., DBU, cesium carbonate, etc.) or inorganic. A "strong base" as used herein is a compound that is capable of deprotonating very weak acids. Examples of strong bases include, but are not limited to, hydroxides, alkoxides, and ammonia.

A "hydroxide" is the commonly known diatomic anion OH$^-$, or a salt thereof (typically an alkali metal or alkaline earth metal salt thereof). Examples of hydroxides include, but are not limited to, sodium hydroxide (NaOH), potassium hydroxide (KOH), lithium hydroxide (LiOH), and calcium hydroxide (Ca(OH)$_2$).

An "alkoxide" is RO$^-$, the conjugate base of an alcohol. Examples include, but are not limited to, methoxide, ethoxide, and propoxide.

An "oxidizing agent" is an agent useful to oxidize a compound, whereby the compound loses electrons or increases its oxidation state. Examples include, but are not limited to, oxygen, ozone, organic peroxides such as hydrogen peroxide, halogens such as fluorine or chlorine, or halogen compounds such as chlorite, chlorate or perchlorate, nitrate compounds such as nitric acid, a sulfuric acid or persulfuric acid, hypohalite compounds such as hypophlorite and sodium hypochlorite (NaClO), hexavalent chromium compounds such as chromic and dichromic acids and chromium trioxide, pyridinium chlorochromate and chromate/dichromate compounds, permanganate compounds, sodium perborate, nitrous oxide, silver oxide, osmium tetroxide, Tollens' reagent, and 2,2'-dipyridyldisulfide.

A "reducing agent" is an agent useful to reduce a compound, whereby the compound gains electrons or decreases its oxidation state. A "hydride reducing agent" is a reducing agent comprising a hydride. Examples include, but are not limited to, sodium borohydride, lithium borohydride, lithium aluminum hydride, lithium tri-butoxyaluminum hydride, diisobutylaluminum hydride (DIBAH), zinc borohydride (See, e.g., Nakata et al., Tett. Lett., 24, 2653-56, 1983), and lithium triethyl borohydride (Super-Hydride®, Sigma-Aldrich, Saint Louis, Mo.). See Seyden-Penne, J. (1997). Reductions by the Alumino- and Borohydrides in Organic Synthesis, 2$^{nd}$ edition. Wiley-VCH.

A "leaving group" is a group or substituent of a compound that can be displaced by another group or substituent in a substitution reaction, such as a nucleophilic substitution reaction. For example, common leaving groups include halo groups; sulfonate ester leaving groups, such as a mesylate (methane sulfonate or —OMs), tosylate (p-toluenesulfonate or —OTs), brosylate, nosylate, besylate (benzene sulfonate) and the like; triflates, such as trifluoromethanesulfonate; and acyloxy groups, such as acetoxy, trifluoroacetoxy and the like. See, e.g., U.S. Pat. No. 8,101,643.

A "lipase" as used herein is an enzyme capable of acylating a steryl glycoside. Examples include, but are not limited to, *Aspergillus* lipase; *Aspergillus niger* lipase; *Thermomyces lanuginosa* lipase; *Candida Antarctica* lipase A; *Candida Antarctica* lipase B; *Candida cylindracae* lipase; *Candida deformans* lipase; *Candida lipolytica* lipase; *Candida parap-*

*silosis* lipase; *Candida rugosa* lipase; *Corynebacterium acnes* lipase; *Cryptococcus* spp. S-2 lipase; *Fusarium cuhnorum* lipase; *Fusarium heterosporum* lipase; *Fusarium oxysporum* lipase; *Mucor javanicus* lipase; *Rhizomucor miehei* lipase; *Rhizomucor delemar* lipase; *Burkholderia* (*Pseudomonas*) *cepacia* lipase; *Pseudomonas camembertii* lipase; *Pseudomonas fluorescens* lipase; *Rhizopus* lipase; *Rhizopus arrhizus* lipase; *Staphylococcus aureus* lipase; *Geotrichium candid* lipase; *Hyphozyma* sp. lipase; *Klebsiella oxytoca* lipase; and homologs thereof (e.g., variants thereof that have an amino acid sequence that is at least 80%, at least 85%; at least 90%, at least 92%; at least 94%; at least 95%, at least 96%; at least 97%; at least 98% or at least 99% identical to any of those wildtype enzymes). See US Patent Application Publication No. 2012/0009659.

A "*Candida Antarctica* lipase" is a lipase originally isolated from *Candida Antarctica* (and now more commonly expressed recombinantly, for example, in an *Aspergillus* species), and may be form A, form B, etc. In some embodiments, the lipase is coupled to a resin (e.g., an acrylic resin). For example, *Candida Antarctica* B lipase is available immobilized on acrylic resin (Novozym® 435, Sigma-Aldrich, Saint Louis, Mo.). In some embodiments, the enzyme is selected from the group consisting of: *Candida Antarctica* lipase A, *Candida Antarctica* lipase B, and homologs thereof (e.g., variants thereof that have an amino acid sequence that is at least 80%, at least 85%; at least 90%, at least 92%; at least 94%; at least 95%, at least 96%; at least 97%; at least 98% or at least 99% identical to any of those wildtype enzymes). See US Patent Application Publication No. 2012/0009659.

"Quenching," as known in the art, refers to stopping or substantially stopping a chemical reaction.

"Catalyze" means to accelerate a reaction by acting as a catalyst. A catalyst is a compound or substance that participates in a chemical reaction but is not consumed by the reaction itself.

Addition of one or more compounds or agents "simultaneously" or "concurrently" means that both are used at the same, or overlapping, times. For example, oxidizing with a first and second oxidizing agent in some embodiments may be accomplished by addition to a reaction vessel through multiple ports at the same or overlapping times.

"Ar" or "aryl" refer to an aromatic carbocyclic moiety having one or more closed rings. Examples include, without limitation, phenyl, naphthyl, anthracenyl, phenanthracenyl, biphenyl, and pyrenyl.

"Heteroaryl" refers to a cyclic moiety having one or more closed rings, with one or more heteroatoms (for example, oxygen, nitrogen or sulfur) in at least one of the rings, wherein at least one of the rings is aromatic, and wherein the ring or rings may independently be fused, and/or bridged. Examples include without limitation quinolinyl, isoquinolinyl, indolyl, furyl, thienyl, pyrazolyl, quinoxalinyl, pyrrolyl, indazolyl, thieno[2,3-c]pyrazolyl, benzofuryl, pyrazolo[1,5-a]pyridyl, thiophenylpyrazolyl, benzothienyl, benzothiazolyl, thiazolyl, 2-phenylthiazolyl, and isoxazolyl.

"Alkyl" or "alkyl group," as used herein, means a straight-chain (i.e., unbranched), branched, or cyclic hydrocarbon chain that is completely saturated. In some embodiments, alkyl groups contain 1, 2, or 3, to 4, 5 or 6 carbon atoms (e.g., $C_{1-4}$, $C_{2-4}$, $C_{3-4}$, $C_{1-5}$, $C_{2-5}$, $C_{3-5}$, $C_{1-6}$, $C_{2-6}$, $C_{3-6}$). In some embodiments, alkyl groups contain 3-4 carbon atoms. In certain embodiments, alkyl groups contain 1-3 carbon atoms. In still other embodiments, alkyl groups contain 2-3 carbon atoms, and in yet other embodiments alkyl groups contain 1-2 carbon atoms. In certain embodiments, the term "alkyl" or "alkyl group" refers to a cycloalkyl group, also known as carbocycle. Non-limiting examples of exemplary alkyl groups include methyl, ethyl, propyl, isopropyl, butyl, cyclopropyl and cyclohexyl.

"Alkenyl" or "alkenyl group" as used herein refers to a straight-chain (i.e., unbranched), branched, or cyclic hydrocarbon chain that has one or more double bonds. In certain embodiments, alkenyl groups contain 2-6 carbon atoms. In certain embodiments, alkenyl groups contain 2-4 carbon atoms. In still other embodiments, alkenyl groups contain 3-4 carbon atoms, and in yet other embodiments alkenyl groups contain 2-3 carbon atoms. According to another aspect, the term alkenyl refers to a straight chain hydrocarbon having two double bonds, also referred to as "diene." In other embodiments, the term "alkenyl" or "alkenyl group" refers to a cycloalkenyl group. Non-limiting examples of exemplary alkenyl groups include —CH═CH₂, —CH₂CH═CH₂ (also referred to as allyl), —CH═CHCH₃, —CH₂CH₂CH═CH₂, —CH₂CH═CHCH₃, —CH═CH₂CH₂CH₃, —CH═CH₂CH═CH₂, and cyclobutenyl.

"Alkoxy" or "alkylthio" as used herein refers to an alkyl group, as previously defined, attached to the principal carbon chain through an oxygen ("alkoxy") or sulfur ("alkylthio") atom.

"Methylene", "ethylene", and "propylene" as used herein refer to the bivalent moieties —CH₂—, —CH₂CH₂—, and —CH₂CH₂CH₂—, respectively.

"Ethenylene", "propenylene", and "butenylene" as used herein refer to the bivalent moieties —CH═CH—, —CH═CHCH₂—, —CH₂CH═CH—, —CH═CHCH₂CH₂—, —CH₂CH═CH₂CH₂—, and —CH₂CH₂CH═CH—, where each ethenylene, propenylene, and butenylene group can be in the cis or trans configuration. In certain embodiments, an ethenylene, propenylene, or butenylene group can be in the trans configuration.

"Alkylidene" refers to a bivalent hydrocarbon group formed by mono or dialkyl substitution of methylene. In certain embodiments, an alkylidene group has 1-6 carbon atoms. In other embodiments, an alkylidene group has 2-6, 1-5, 2-4, or 1-3 carbon atoms. Such groups include propylidene (CH₃CH₂CH═), ethylidene (CH₃CH═), and isopropylidene (CH₃(CH₃)CH═), and the like.

"Alkenylidene" refers to a bivalent hydrocarbon group having one or more double bonds formed by mono or dialkenyl substitution of methylene. In certain embodiments, an alkenylidene group has 2-6 carbon atoms. In other embodiments, an alkenylidene group has 2-6, 2-5, 2-4, or 2-3 carbon atoms. According to one aspect, an alkenylidene has two double bonds. Exemplary alkenylidene groups include CH₃CH═C═, CH₂═CHCH═, CH₂═CHCH₂CH═, and CH₂═CHCH₂CH═CHCH═.

"$C_{1-6}$ alkyl ester or amide" refers to a $C_{1-6}$ alkyl ester or a $C_{1-6}$ alkyl amide where each $C_{1-6}$ alkyl group is as defined above. Such $C_{1-6}$ alkyl ester groups are of the formula ($C_{1-6}$ alkyl)OC(═O)— or ($C_{1-6}$ alkyl)C(═O)O—. Such $C_{1-6}$ alkyl amide groups are of the formula ($C_{1-6}$ alkyl)NHC(═O)— or ($C_{1-6}$ alkyl)C(═O)NH—, "$C_{2-6}$ alkenyl ester or amide" refers to a $C_{2-6}$ alkenyl ester or a $C_{2-6}$ alkenyl amide where each $C_{2-6}$ alkenyl group is as defined above. Such $C_{2-6}$ alkenyl ester groups are of the formula ($C_{2-6}$ alkenyl)OC(═O)— or ($C_{2-6}$ alkenyl)C(═O)O—. Such $C_{2-6}$ alkenyl amide groups are of the formula ($C_{2-6}$ alkenyl)NHC(═O)— or ($C_{2-6}$ alkenyl)C(═O)NH—.

"Halo" refers to fluoro, chloro, bromo or iodo,

"Haloalkyl" refers to an alkyl group substituted with one or more halo atoms. For example, "fluoromethyl" refers to a methyl group substituted with one or more fluoro atoms (e.g., monofluoromethyl, difluoromethyl, trifluoromethyl).

"Hydroxyalkyl" refers to an alkyl group substituted with a hydroxyl group (—OH).

"Fluoromethoxy" as used herein refers to a fluoromethyl group, as previously defined, attached to the principal carbon chain through an oxygen atom.

"Thiol" refers to an organosulfur compound R—SH, wherein R is an aliphatic group.

"Cyano" refers to the group —C≡N, or —CN.

"Aliphatic" is an acyclic or cyclic, non-aromatic carbon compound.

"Protecting group" as used herein, is meant that a particular functional moiety, e.g., O, S, or N, is temporarily blocked so that a reaction can be carried out selectively at another reactive site in a multifunctional compound. For example, in certain embodiments, as detailed herein, certain exemplary oxygen protecting groups are utilized. Oxygen protecting groups include, but are not limited to, groups bonded to the oxygen to form an ether, such as methyl, substituted methyl (e.g., Trt (triphenylmethyl), MOM (methoxymethyl), MTM (methylthiomethyl), BOM (benzyloxy)ethyl), PMBM or MPM (p-methoxybenzyloxymethyl)), substituted ethyl (e.g., 2-(trimethylsilyl)ethyl), benzyl, substituted benzyl (e.g., para-methoxybenzyl), silyl (e.g., TMS (trimethylsilyl), TES (triethylsilyl), TIPS (triisopropylsilyl), TBDMS (t-butyldimethylsilyl), tribenzylsilyl, TBDPS (t-butyldiphenyl silyl), 2-trimethylsilylprop-2-enyl, t-butyl, tetrahydropyranyl, allyl, etc.

In some embodiments, the compounds described herein may be provided as a salt, such as a pharmaceutically acceptable salt. "Pharmaceutically acceptable salts" are salts that retain the desired biological activity of the parent compound and do not impart undesired toxicological effects. Specific examples of pharmaceutically acceptable salts include inorganic acid salts (such as sulfates, nitrates, perchlorates, phosphates, carbonates, bicarbonates, hydrofluorides, hydrochlorides, hydrobromides and hydroiodides), organic carboxylates (such as acetates, oxalates, maleates, tartrates, fumarates and citrates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

Unless indicated otherwise, nomenclature used to describe chemical groups or moieties as used herein follow the convention where, reading the name from left to right, the point of attachment to the rest of the molecule is at the right-hand side of the name. For example, the group "($C_{1-3}$ alkoxy)$C_{1-3}$ alkyl," is attached to the rest of the molecule at the alkyl end. Further examples include methoxyethyl, where the point of attachment is at the ethyl end, and methylamino, where the point of attachment is at the amine end.

Unless indicated otherwise, where a mono or bivalent group is described by its chemical formula, including one or two terminal bond moieties indicated by "—," it will be understood that the attachment is read from left to right.

Unless otherwise stated, structures depicted herein are also meant to include all enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

B. COMPOUNDS AND CHEMICAL SYNTHESIS

Provided herein are compounds (e.g., intermediate compounds) and methods that are useful for the preparation of compounds useful as orexin-2 receptor antagonists, such as (1R,2S)-2-(((2,4-dimethylpyrimidin-5-yl)oxy)methyl)-2-(3-fluorophenyl)-N-(5-fluoropyridin-2-yl)cyclopropanecarboxamide (Compound A, below), which have been found to be potent orexin receptor antagonists, and may be useful in the treatment of sleep disorders such as insomnia, as well as for other therapeutic uses.

Compound A

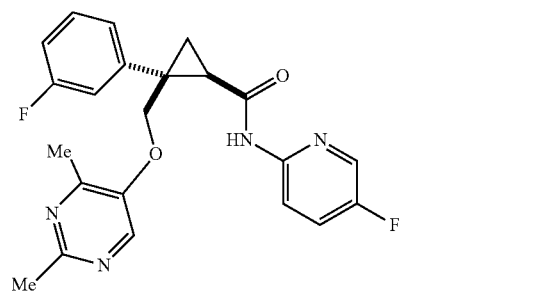

However, it will be understood that the compounds and methods herein may also be useful to make similar compounds and/or perform similar chemical syntheses.

Provided is a process for making a compound of Formula I,

I

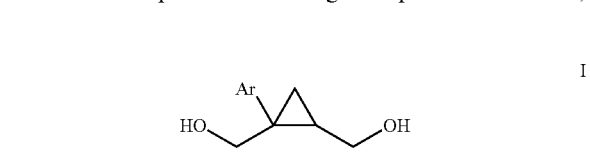

wherein Ar is an aryl such as phenyl, which aryl may be unsubstituted, or substituted 1-3 times, for example, with substituents independently selected from the group consisting of: halo, $C_{1-6}$alkyl, $C_{1-6}$alkoxy, and halo$C_{1-6}$alkyl, the method comprising one or more of the steps of:

i) providing a composition comprising a compound of Formula II:

II

wherein Ar is as given above, and an organic solvent, wherein said composition is at a temperature of from −30 to 40° C., or from −30 to 30° C., or from −30 to 10° C., or from −10 to 0° C., or from −10 to −5° C.; and ii) adding to said composition a hydride reducing agent, wherein said agent reduces said compound of Formula II into said compound of Formula I, to thereby make said compound of Formula I.

In some embodiments, Ar is phenyl, which phenyl may be unsubstituted, or substituted 1-3 times with a halo independently selected from the group consisting of: chloro, fluoro, bromo, and iodo.

In some embodiments, the organic solvent is an aromatic hydrocarbon solvent, an aliphatic hydrocarbon solvent, a halogenated hydrocarbon solvent or an ether solvent.

In some embodiments, the process may further include the step of mixing (e.g., by stirring) the composition after said adding step for a time of 12 to 24 hours.

In some embodiments, the process may further include the step of quenching the reduction by adding to said composition a mild aqueous acid (e.g., citric acid, EDTA or tartaric acid).

In some embodiments, the compound of Formula II has the absolute stereochemistry of Formula IIa:

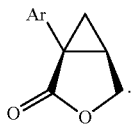

IIa

In some embodiments, the compound of Formula II has an enantiomeric excess (ee) of the Formula IIa stereoisomer of at least 75, 80, 85, 90, 95, 98, 99%, or greater.

In some embodiments, the compound of Formula II or Formula IIa is the compound:

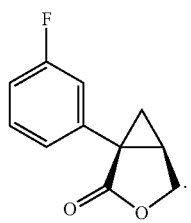 [SMILES: O=C1OC[C@@H]2C[C@]12c1cccc(F)c1]

In some embodiments, the compound of Formula I has the absolute stereochemistry of Formula Ia:

Ia

In some embodiments, the compound of Formula I has an enantiomeric excess (ee) of the Formula Ia stereoisomer of at least 75, 80, 85, 90, 95, 98, 99%, or greater.

In some embodiments, the compound of Formula I or Formula Ia is:

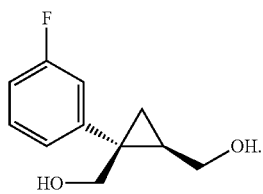

Also provided is compound of Formula III:

III wherein Ar is an aryl such as phenyl, which aryl may be unsubstituted, or substituted 1-3 times, for example with substituents independently chosen from the group consisting of: halo, $C_{1-6}$alkyl, $C_{1-6}$alkoxy, and halo$C_{1-6}$alkyl.

In some embodiments, Ar is phenyl, which phenyl may be unsubstituted, or substituted 1-3 times with a halo independently selected from the group consisting of: chloro, fluoro, bromo, and iodo.

In some embodiments, the compound is:

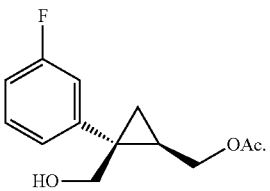 [SMILES: CC(=O)OC[C@@H]1C[C@@]1(CO)c1cccc(F)c1]

Also provided is a process for making a compound of Formula III:

III wherein Ar is aryl such as phenyl, which aryl may be unsubstituted, or substituted 1-3 times, for example with substituents independently selected from the group consisting of: halo, $C_{1-6}$alkyl, $C_{1-6}$alkoxy, and halo$C_{1-6}$alkyl, comprising reacting a mixture of:
i) a compound of Formula Ia:

Ia wherein Ar is as given above,
ii) vinyl acetate,
iii) a lipase, and
iv) an organic solvent
for a time of from 5 to 36 hours, or from 7 to 18 hours, to thereby make the compound of Formula III.

In some embodiments, Ar is phenyl, which phenyl may be unsubstituted, or substituted 1-3 times with a halo independently selected from the group consisting of: chloro, fluoro, bromo, and iodo.

In some embodiments, the organic solvent is tetrahydrofuran, 2-methyltetrahydrofuran, an ether solvent, acetone, or acetonitrile.

In some embodiments, the lipase is a *Candida Antarctica* lipase, for example, a *Candida Antarctica* B lipase, which may be coupled to solid support such as an acrylic resin.

In some embodiments, the process may further include the step of filtering the mixture after said reacting to produce a filtrate, and may also include concentrating the filtrate to produce a concentrated filtrate. In some embodiments, the process may further include the step of washing the concentrated filtrate with water or water comprising a salt (e.g., a solution of 15-20% NaCl in water).

Also provided is a compound of Formula IV:

IV wherein:
Ar is an aryl such as phenyl, which aryl may be unsubstituted, or substituted 1-3 times, for example with substituents independently selected from the group consisting of: halo, $C_{1-6}$alkyl, $C_{1-6}$alkoxy, and halo$C_{1-6}$alkyl; and $R_1$ is a leaving group.

In some embodiments, Ar is phenyl, which phenyl may be unsubstituted, or substituted 1-3 times with a halo independently selected from the group consisting of: chloro, fluoro, bromo, and iodo.

In some embodiments, the leaving group is a sulfonate ester leaving group selected from the group consisting of: mesylate, tosylate, nosylate, benzene sulfonate, and brosylate.

In some embodiments, the compound is:

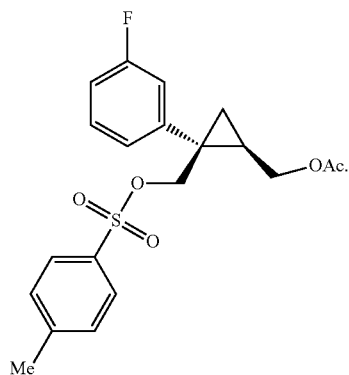 [SMILES: CC(=O)OC[C@@H]1C[C@@]1(COS(=O)(=O)c1ccc(C)cc1)c1cccc(F)c1]

In some embodiments, the compound of Formula IV has the absolute stereochemistry of Formula IVa:

IVa

In some embodiments, the compound of Formula IV has an enantiomeric excess (ee) of the Formula IVa stereoisomer of at least 75, 80, 85, 90, 95, 98, 99%, or greater.

Further provided is a process for making a compound of Formula IV:

IV wherein Ar is an aryl such as phenyl, which aryl may be unsubstituted, or substituted 1-3 times, for example with substituents independently selected from the group consisting of: halo, $C_{1-6}$alkyl, $C_{1-6}$alkoxy, and halo$C_{1-6}$alkyl; and $R_1$ is a sulfonate ester leaving group, said process comprising reacting a compound of Formula III:

III wherein Ar is as given above, with a compound selected from the group consisting of: tosyl chloride, mesyl chloride, nosyl chloride, toluenesulfonyl chloride, toluenesulfonic anhydride and methanesulfonic anhydride, wherein said reacting is carried out in an organic solvent in the presence of a base, to thereby make said compound of Formula IV.

In some embodiments, Ar is phenyl, which phenyl may be unsubstituted, or substituted 1-3 times with a halo independently selected from the group consisting of: chloro, fluoro, bromo, and iodo.

In some embodiments, the reacting is carried out for a time of from 10 minutes to 2 hours.

In some embodiments, the base is an organic amine or potassium carbonate.

In some embodiments, the compound of Formula III is:

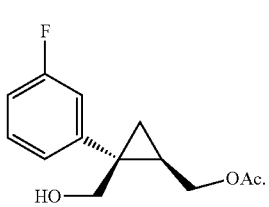 [SMILES: CC(=O)OC[C@@H]1C[C@@]1(CO)c1cccc(F)c1]

In some embodiments, the compound of Formula IV has the absolute stereochemistry of Formula IVa:

IVa

In some embodiments, the compound of Formula IV has an enantiomeric excess (ee) of the Formula IVa stereoisomer of at least 75, 80, 85, 90, 95, 98, 99%, or greater.

Also provided is a process for making a compound of Formula V,

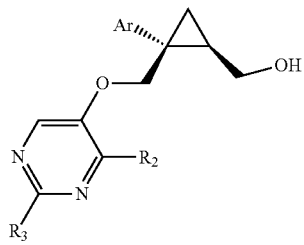

wherein Ar is an aryl such as phenyl, which aryl may be unsubstituted, or substituted 1-3 times, for example with substituents independently selected from the group consisting of: halo, $C_{1-6}$alkyl, $C_{1-6}$alkoxy, and halo$C_{1-6}$alkyl; and $R_2$ and $R_3$ are each independently selected from the group consisting of: hydrogen, $C_{1-6}$alkyl, halo$C_{1-6}$ alkyl, $C_{1-6}$alkoxy, and hydroxy$C_{1-6}$alkyl, comprising the steps of:
a) stirring a mixture of:
i) a compound of Formula IV:

wherein Ar is as given above; and
$R_1$ is a leaving group,
ii) a substituted pyrimidine of Formula VI:

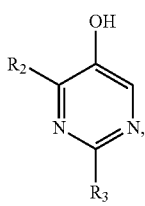

wherein $R_2$ and $R_3$ are as given above;
iii) a base; and
iv) an organic solvent,
at a temperature of from 65-70° C., for 1 to 12 hours; and then
b) reacting the mixture with an aqueous base for a time of from 2 to 20 hours,
to thereby make said compound of Formula V.

In some embodiments, Ar is phenyl, which phenyl may be unsubstituted, or substituted 1-3 times with a halo independently selected from the group consisting of: chloro, fluoro, bromo, and iodo.

In some embodiments, $R_2$ and $R_3$ are each independently selected from the group consisting of: hydrogen and $C_{1-6}$alkyl.

In some embodiments, the compound of Formula IV has the absolute stereochemistry of Formula IVa:

In some embodiments, the compound of Formula IV has an enantiomeric excess (ee) of the Formula IVa stereoisomer of at least 75, 80, 85, 90, 95, 98, 99%, or greater.

Further provided is a process for making a compound of Formula VI:

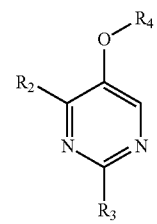

wherein $R_2$ and $R_3$ are each independently selected from the group consisting of: hydrogen and $C_{1-6}$ alkyl,
comprising the step of heating a mixture of:
i) a compound of Formula B:

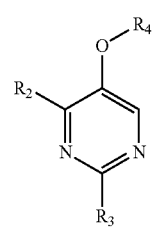

wherein:
$R_2$ and $R_3$ are as given above; and
$R_4$ is $C_{1-6}$ alkyl,
ii) an alkoxide or hydroxide salt,
iii) a thiol, and
iv) an organic solvent,
to thereby make said compound of Formula VI, In some embodiments, the heating is to a temperature of from 50 to 140° C. In some embodiments, heating comprises boiling or refluxing the mixture.

In some embodiments, the heating is carried out in a time of from 5 to 50 hours.

Also provided is a process for making a compound of Formula B:

wherein:
R$_2$ and R$_3$ are each independently selected from the group consisting of hydrogen and C$_{1-6}$ alkyl; and
R$_4$ is C$_{1-6}$ alkyl,
comprising mixing:
 i) a compound of Formula A:

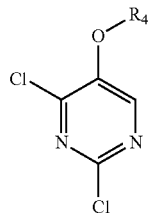

A wherein R$_4$ is as given above,
 ii) trimethylaluminum,
 iii) a palladium catalyst, and
 iv) an organic solvent,
to thereby make said compound of Formula B.

In some embodiments, the mixing step is carried out for a time of from 12 to 48 hours.

In some embodiments, the mixing step is carried out at a temperature of from 20 to 110° C.

Further provided is a process for making a compound of Formula B:

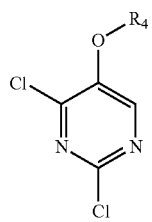

B wherein:
R$_2$ and R$_3$ are each independently selected from the group consisting of hydrogen and C$_{1-6}$ alkyl; and
R$_4$ is C$_{1-6}$ alkyl,
comprising mixing:
 i) a compound of Formula A:

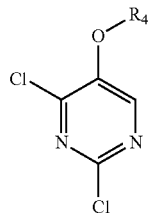

A wherein R$_4$ is as given above,
 ii) a nickel catalyst (e.g., Ni(acac)$_2$, Ni(PPh$_3$)$_2$Cl$_2$, or Ni(dppp)Cl$_2$),
 iii) an alkylmagnesium halide, and
 iv) an organic solvent,
to thereby make said compound of Formula B.

In some embodiments, the mixing is carried out for a time of from 6 to 36 hours.

In some embodiments, the mixing is carried out at a temperature of from 10 to 30° C.

Also provided is a process for making a compound of Formula VII:

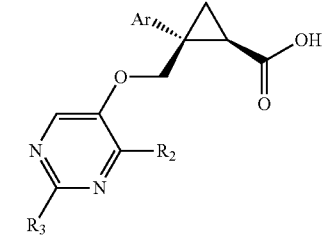

VII wherein Ar is an aryl such as phenyl, which aryl may be unsubstituted, or substituted 1-3 times, for example with substituents independently selected from the group consisting of: halo, C$_{1-6}$alkyl, C$_{1-6}$alkoxy, and haloC$_{1-6}$alkyl; and
R$_2$ and R$_3$ are each independently selected from the group consisting of: hydrogen, C$_{1-6}$alkyl, haloC$_{1-6}$ alkyl, C$_{1-6}$alkoxy, and hydroxyC$_{1-6}$alkyl,
comprising the steps of
 a) oxidizing a compound of Formula V:

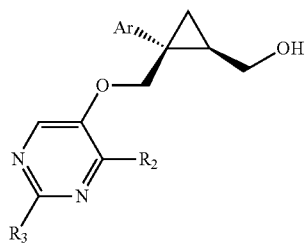

V wherein Ar, R$_2$ and R$_3$ are as given above,
with a first oxidizing agent, to form an aldehyde of Formula VIII:

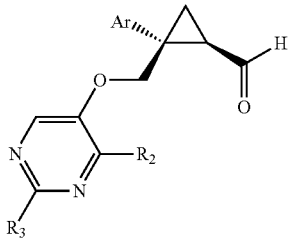

VIII wherein Ar, R$_2$ and R$_3$ are as given above; and then
 b) oxidizing the aldehyde of Formula VIII with a second oxidizing agent,
to thereby make said compound of Formula VII.

In some embodiments, Ar is phenyl, which phenyl may be unsubstituted, or substituted 1-3 times with a halo independently selected from the group consisting of: chloro, fluoro, bromo, and iodo.

In some embodiments, R$_2$ and R$_3$ are each independently selected from the group consisting of: hydrogen and C$_{1-6}$alkyl.

In some embodiments, the first oxidizing agent is sodium hypochlorite.

In some embodiments, oxidizing of step a) is catalyzed with an effective amount of 2,2,6,6-tetramethylpiperidine 1-oxyl (TEMPO).

In some embodiments, the second oxidizing agent is sodium chlorite.

In some embodiments, the first oxidizing agent and the second oxidizing agent are the same. In some embodiments, the first oxidizing agent and the second oxidizing agent are different.

Further provided is a process for preparing a compound of Formula VII,

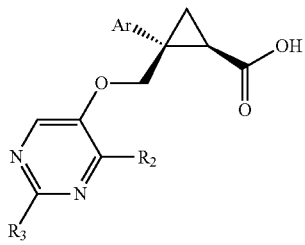

VII wherein Ar is an aryl such as phenyl, which aryl may be unsubstituted, or substituted 1-3 times, for example with substituents independently selected from the group consisting of: halo, $C_{1-6}$alkyl, $C_{1-6}$alkoxy, and halo$C_{1-6}$alkyl; and $R_2$ and $R_3$ are each independently selected from the group consisting of: hydrogen, $C_1$ halo$C_{1-6}$ alkyl, $C_{1-6}$alkoxy, and hydroxy$C_{1-6}$alkyl, comprising: oxidizing a compound of Formula V:

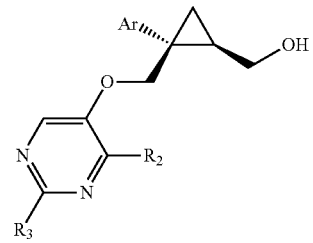

V wherein Ar, $R_2$ and $R_3$ are as given above, with sodium hypochlorite and sodium chlorite, to thereby make said compound of Formula VII.

In some embodiments, Ar is phenyl, which phenyl may be unsubstituted, or substituted 1-3 times with a halo independently selected from the group consisting of: chloro, fluoro, bromo, and iodo.

In some embodiments, $R_2$ and $R_3$ are each independently selected from the group consisting of: hydrogen and $C_{1-6}$alkyl.

In some embodiments, the oxidizing with sodium hypochlorite and sodium chlorite is carried out simultaneously.

In some embodiments, the oxidizing is catalyzed with an effective amount of TEMPO.

Also provided is a process for making a compound of Formula IX:

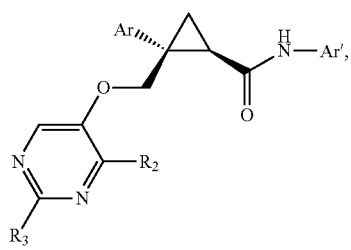

IX wherein:

Ar is an aryl such as phenyl, which aryl may be unsubstituted, or substituted 1-3 times, for example with substituents independently selected from the group consisting of: halo, $C_{1-6}$ alkyl, $C_{1-6}$alkoxy, and halo$C_{1-6}$alkyl;

$R_2$ and $R_3$ are each independently selected from the group consisting of: hydrogen, $C_{1-6}$alkyl, halo$C_{1-6}$ alkyl, $C_{1-6}$alkoxy, and hydroxy$C_{1-6}$alkyl; and Ar' is a pyridine group:

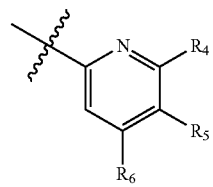

wherein:

$R_4$ is selected from the group consisting of: hydrogen, halo, $C_{1-6}$alkyl, $C_{1-6}$alkoxy, and ($C_{1-6}$alkoxy)$C_{1-6}$alkyl;

$R_5$ is selected from the group consisting of: hydrogen, halo, $C_{1-6}$alkyl, and halo$C_{1-6}$alkyl; and $R_6$ is selected from the group consisting of: hydrogen, halo, $C_{1-6}$alkyl, halo$C_{1-6}$alkyl, $C_{1-6}$alkoxy, ($C_{1-6}$alkoxy)$C_{1-6}$alkyl, and cyano;

comprising the step of reacting a compound of Formula VII:

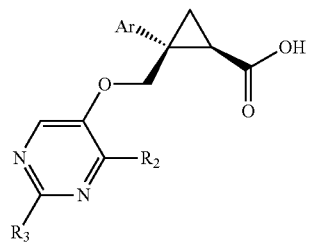

VII wherein Ar, $R_2$ and $R_3$ are as given above, with a compound of Formula X:

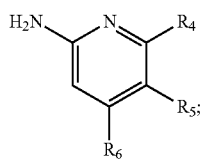

X wherein $R_4$, $R_5$, and $R_6$ are as given above, said reacting carried out in an organic solvent in the presence of an organic amine and an amide coupling agent, to prepare said compound of Formula IX.

In some embodiments, Ar is phenyl, which phenyl may be unsubstituted, or substituted 1-3 times with a halo independently selected from the group consisting of: chloro, fluoro, bromo, and iodo.

In some embodiments, $R_2$ and $R_3$ are each independently selected from the group consisting of: hydrogen and $C_{1-6}$alkyl.

It should be understood that any of the compounds listed above and used in the processes disclosed herein may be provided in a stereochemically pure form and are included in the present disclosure. In some embodiments, the stereochemically pure compound has greater than about 75% by weight of one stereoisomer of the compound and less than about 25% by weight of other stereoisomers of the compound, greater than about 80% by weight of one stereoisomer of the compound and less than about 20% by weight of other stereoisomers of the compound, or greater than about 85% by weight of one stereoisomer of the compound and less than about 15% by weight of other stereoisomers of the compound, or greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 98% by weight of one stereoisomer of the compound and less than about 2% by weight of the other stereoisomers of the compound. In some embodiments, the stereochemically pure compound has greater than 99% by weight of one stereoisomer of the compound and less than 1% by weight of the other stereoisomers of the compound.

As noted above, in some embodiments the compounds described herein may be provided as a salt, such as a pharmaceutically acceptable salt.

Examples

General

Column chromatography was carried out using a Biotage SP4. Solvent removal was carried out using either a Büchii rotary evaporator or a Genevac centrifugal evaporator. Preparative LC/MS was conducted using a Waters autopurifier and 19×100 mm XTerra 5 micron MS C18 column under acidic mobile phase conditions. NMR spectra were recorded using either a Varian 400 or 500 MHz spectrometer.

The term "inerted" is used to describe a reactor (e.g., a reaction vessel, flask, glass reactor, and the like) in which the air in the reactor has been replaced with an essentially moisture-free or dry, inert gas (such as nitrogen, argon, and the like). The term "equivalent" (abbreviation: equiv.) as used herein describes the stoichiometry (molar ratio) of a reagent or a reacting compound by comparison to a pre-established starting material. The term "weight" (abbreviation: wt) as used herein corresponds to the ratio of the mass of a substance or a group of substances by comparison to the mass of a particular chemical component of a reaction or purification specifically referenced in the examples below. The ratio is calculated as: g/g, or Kg/Kg. The term "volume" (abbreviation: vol) as used herein corresponds to the ratio of the volume of a given substance or a group of substances to the mass or volume of a pre-established chemical component of a reaction or purification. The units used in the equation involve matching orders of magnitude. For example, a ratio is calculated as: mL/mL, mL/g, L/L or L/Kg.

General methods and experimentals for preparing compounds of the present invention are set forth below. In certain cases, a particular compound is described by way of example. However, it will be appreciated that in each case a series of compounds of the present invention were prepared in accordance with the schemes and experimentals described below.

The following abbreviations are used herein:

| Abbreviation | Definition |
| --- | --- |
| TMS | Trimethylsilyl |
| TBAF | Tetrabutylammonium fluoride |
| NaOH | Sodium hydroxide |
| $Bu_4N\ HSO_4$ | Tetrabutylammonium hydrogen sulfate |
| THF | Tetrahydrofuran |
| rt | Room temperature |
| h | Hour(s) |
| NaCl | Sodium chloride |
| HCOOH | Formic acid |
| V | Volumes |
| equiv. | Equivalent(s) |
| wt | Weights |
| CDI | N,N-Carbonyldiimidazole |
| DCM | Dichloromethane |
| Aq | Aqueous |
| Sat. | Saturated |
| HCl | Hydrochloric acid |
| HRMS | High Resolution Mass Spectrometry |
| nBuLi | n-butyl lithium |
| $NH_4Cl$ | Ammonium chloride |
| MeOH | Methanol |
| EtOAc | Ethyl acetate |
| $NaHCO_3$ | Sodium bicarbonate |
| M | Molar (moles/liter) |
| T | Temperature |
| MTBE | Methyl tert-butyl ether |
| TLC | Thin layer chromatography |
| N | Normal (equivalents per liter) |
| iPrMgBr | Isopropyl magnesium bromide |
| LiCl | Lithium chloride |
| NaOAc | Sodium acetate |
| $NH_4OH$ | Ammonium hydroxide |
| HPLC | High performance liquid chromatography |
| ee | Enantiomeric excess |
| DMI | 1,3-Dimethyl-2-imidazolidinone |
| UV | Ultraviolet |
| RRT | Relative retention time |
| OROT | Optical rotation |
| Bz | Benzoyl |
| ACN | Acetonitrile |
| ®T3P (Archimica, Germany) | Tri-n-propyl phosphonic acid anhydride |
| HATU | N,N,N',N'-tetramethyl-O-(7-azabenzotriazol-1-yl)uronium hexafluorophosphate |

A. Preparation of Cyclopropane Compounds of Formula II

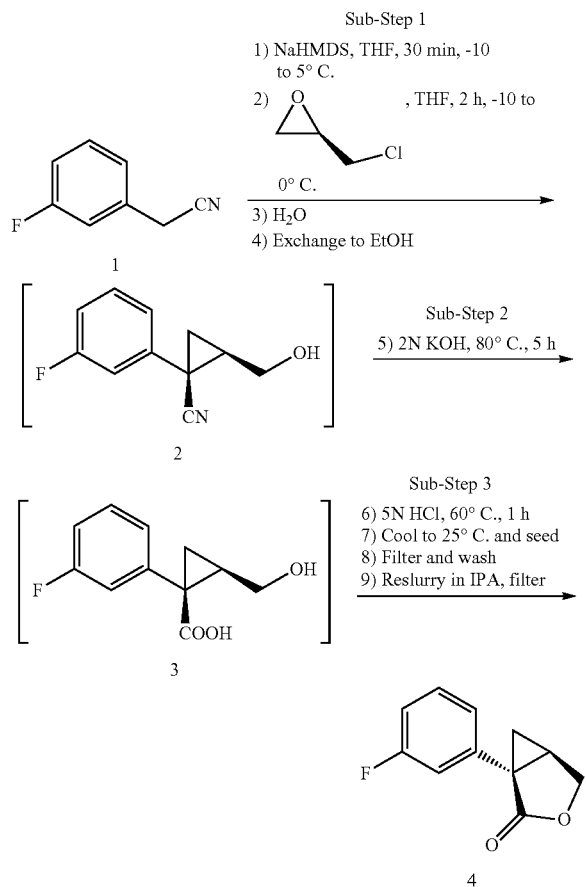

(1S,5R)-1-(3-fluorophenyl)-3-oxabicyclo[3.1.0]
hexan-2-one (4)

3-fluorophenylacetonitrile (1, 200 g, 1.48 mol, 1.0 equiv.) was dissolved in THF (1500 mL) and cooled to −3° C. To the solution was added dropwise sodium bis(trimethylsilyl)amine (2.0 M solution in THF, 1520 mL, 3.04 mol, 2.05 equiv.), maintaining the internal temperature at less than 7° C. The mixture was allowed to stir for 29 h at 0° C. after which it was warmed to room temperature and quenched by addition of water (85 mL). The mixture was concentrated to near dryness by rotary evaporation and ethanol (1500 mL) was added followed by aqueous potassium hydroxide solution (2.0 M, 1477 mL). The mixture was heated to 80° C. and aged at this temperature for 5 hours, after which it was cooled to room temperature. Aqueous hydrochloric acid solution (6 M, 944 mL) and water (189 mL) were added. The mixture was heated to 60° C. and aged at this temperature for 2 hours. The mixture was cooled to room temperature and seed crystals of 4 ((1S,5R)-1-(3-fluorophenyl)-3-oxabicyclo[3.1.0]hexan-2-one) were added (1.5 g, 0.005 equiv.). The resulting slurry was allowed to stir overnight and then filtered. The cake was washed with 2:1 water/ethanol solution (2×200 mL) followed by water (3×400 mL) until the pH of the filtrate was pH=7. The cake was dried under vacuum with a sweep of nitrogen to afford (1S,5R)-1-(3-fluorophenyl)-3-oxabicyclo[3.1.0]hexan-2-one (4, 205.31 g, 70% yield, 91% ee) as an off-white crystalline solid.

(1S,5R)-1-(3-fluorophenyl)-3-oxabicyclo[3.1.0]hexan-2-one: $^1$H NMR (500 MHz, DMSO-$d_6$) δ 7.43-7.36 (m, 1H), 7.35-7.31 (m, 1H), 7.31-7.28 (m, 1H), 7.14-7.08 (m, 1H), 4.46 (dd, J=9.1, 4.6 Hz, 1H), 4.25 (d, J=9.1 Hz, 1H), 2.80 (dt, J=8.0, 4.6 Hz, 1H), 1.72 (dd, J=7.9, 4.8 Hz, 1H), 1.37 (t, J=4.8 Hz, 1H); $^{13}$C NMR (126 MHz, DMSO-$d_6$) δ 175.35, 161.98 (d, $J_{CF}$=243.1 Hz), 137.67 (d, $J_{CF}$=8.2 Hz), 130.15 (d, $J_{CF}$=8.6 Hz), 124.19 (d, $J_{CF}$=2.8 Hz), 115.01 (d, $J_{CF}$=22.4 Hz), 113.95 (d, $J_{CF}$=20.9 Hz), 67.93, 30.70 (d, $J_{CF}$=2.4 Hz), 25.57, 19.99.

HRMS Calculated for $C_{11}H_{10}FO_2$ $[M+H]^+$ 193.0665. found 193.0659.

HPLC Method TM-1172 for Monitoring of Above Process Step:

Equipment, Reagents, and Mobile Phase:

Equipment:
  HPLC column: Waters SunFire C18, 3.5 um 3×150 mm, Waters catalog no. 186002544.
  Solvent Delivery System Agilent 1100 HPLC quaternary pump, low pressure mixing, with an in-line degasser, or equivalent.
  Autosampler: Agilent 1100 autosampler, variable loop, 0.1 to 100 μL range, or equivalent.
  Detector: Agilent 1100 Diode Array Detector or equivalent.
  Chromatographic Agilent ChemStation software version A.09.03 or
  Software: higher for HPLC, Waters Empower 2 Build 2154, or equivalent.
  Volumetric Glassware: Class A.
  Balance: Analytical balance, capable of weighing±0.1 mg.

Reagents:
  Water: HPLC grade, (Baker cat no. 4218-03) or equivalent
  Acetonitrile: HPLC grade, (Baker cat no. 9017-03) or equivalent.
  Trifluoroacetic acid (TFA): Spectrophotometric grade, Aldrich (catalog no. 302131) or equivalent.

Mobile Phase:
  Solvent A: Add 1000 mL of water to an appropriate flask. Add 1.0 mL of trifluouroacetic acid and mix. Degas in-line during use.
  Solvent B: Add 1000 mL of acetonitrile to an appropriate flask. Add 1.0 mL of trifluouroacetic acid and mix. Degas in-line during use.

HPLC Parameters:

Chromatographic Parameters

| HPLC column: | Waters SunFire C18, 3.5 um 3 × 150 mm, Waters catalog no. 186002544. | | |
|---|---|---|---|
| Temperature: | 40° C. | | |
| Flow rate: | 0.5 mL/min. Flow rate may be adjusted ±0.2 mL/min to obtain specified retention times. | | |
| | Time, min | %-Solvent A | %-Solvent B |
| Gradient: | Initial | 95 | 5 |
| | 3 | 70 | 30 |
| | 20 | 70 | 30 |
| | 20.1 | 95 | 5 |
| | 30 | 95 | 5 |
| Injection volume: | 5 μL | | |
| Detection: | 210 nm UV | | |

-continued

| | |
|---|---|
| Data acquisition time: | 20 min |
| Run time: | 30 min |

TM-1213: Chiral HPLC Assay for 4
Equipment, Reagents, and Mobile Phase:
Equipment:

| | |
|---|---|
| HPLC column: | AD-H 4.6 × 250 mm 5 μm, Chiral Tech catalog no. 19325 or equivalent. |
| Solvent Delivery System: | Agilent 1100 HPLC quaternary pump, low pressure mixing with an in-line degasser, or equivalent. |
| Autosampler: | Agilent 1100 autosampler, 0.1 to 100 μL range, or equivalent. |
| Detector: | Agilent 1100 variable wavelength detector or equivalent. |
| Chromatographic Software: | Agilent ChemStation software version A.09.03 or higher for HPLC, Waters Empower 2 Build 2154, or equivalent. |
| Volumetric Glassware: | Class A. |
| Volumetric pipette: | Class A. |
| Balance: | Analytical balance, capable of weighing ± 0.1 mg. |

Reagents:

| | |
|---|---|
| Hexanes: | HPLC grade, EMD (catalog no. HX0296-1) or equivalent. |
| 2-Propanol: | HPLC grade, J. T. Baker (catalog no. 9095-03) or equivalent. |

Mobile Phase:
Mobile phase A:
Using appropriate graduated cylinders, add 900 mL of hexanes and 100 mL of 2-propanol to an appropriate flask. Mix well and degas in line during use.
HPLC Parameters:
Chromatographic Parameters:

| | |
|---|---|
| HPLC column: | AD-H 4.6 × 250 mm 5 μM, Chiral Tech catalog no, 19325 or equivalent. |
| Temperature: | 25° C. |
| Flow rate: | 1.0 mL/min. Flow rate may be adjusted to obtain specified retention times. |
| Isocratic | Mobile Phase A |
| Injection volume: | 5.0 μL |
| Detection: | UV detector 213 nm |
| Acquisition time: | 15 min |
| Re-equilibration time: | N/A |
| Total run time: | 15 min |

Calculations:
The system suitability tests must pass all acceptance criteria before analysis of the results from the Sample Analysis section is allowed to proceed.
%-Enantiomeric Excess Calculation:
Calculate the %-enantiomeric excess (%-ee) for each 4 sample preparation using the appropriate peak areas obtained from each sample analysis injection and the following equation:

$$\% \ ee = \frac{(A_4 - A_{19})(100\%)}{(A_4 + A_{19})}$$

$A_4$ = Peak area of 4 from each sample solution injection $A_{19}$ = Peak area of 19 from each sample solution injection Note: Compound 19 is the enantiomer of compound 4. An enantiomeric excess was calculated at 91% for compound 4.

B. Preparation of Compounds of Formula I

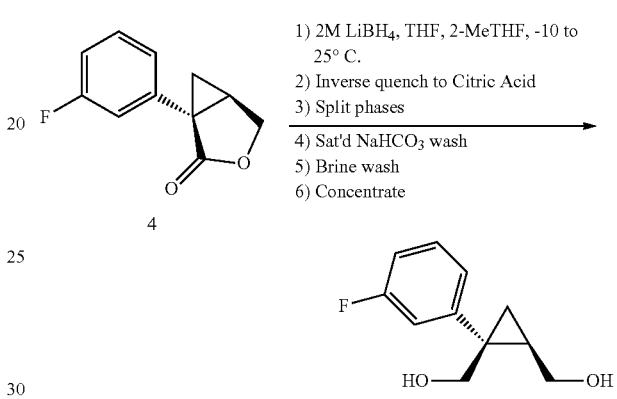

((1S,2R)-1-(3-fluorophenyl)cyclopropane-1,2-diyl)dimethanol (5)

(1S,5R)-1-(3-fluorophenyl)-3-oxabicyclo[3.1.0]hexan-2-one (4, 10.08 g, 0.052 mol, 1.0 equiv.) was dissolved in 2-methyl-THF (75.60 mL) under nitrogen. The solution was cooled to −5 to −10° C., and 2.0 M Lithium tetrahydroborate in THF (39.34 mL, 0.079 mol, 1.5 equiv.) was added to the reaction mixture while maintaining the internal temperature below 0° C. The reaction was stirred at 20-25° C. for 14-16 hours and monitored by HPLC and TLC (EtOAc/Heptane=1/1). Once the reaction was completed, the reaction mixture was cooled to 0-5° C. and reverse quenched into a pre-cooled (0-5° C.) 20% aqueous citric acid solution (50.40 mL, 1.67 equiv.) at such a rate as to maintain the internal temperature below 5° C. Once the quench was complete, the reaction mixture was warmed to 20-25° C. and stirred for at least 20 min. The aqueous layer was back extracted once with 2-methyl-THF (50.40 mL). The organic layers were combined and washed once with saturated aqueous sodium bicarbonate solution (20.16 mL) and once with 20% aqueous NaCl (20.16 mL). The solvent was removed under reduced pressure then azeotroped with 2-methyl-THF until KF is less than 1500 ppm to afford the title compound, ((1S,2R)-1-(3-fluorophenyl)cyclopropane-1,2-diyl)dimethanol; 5 (10.29 g).

((1S,2R)-1-(3-fluorophenyl)cyclopropane-1,2-diyl)dimethanol: $^1$H NMR (500 MHz, CD$_3$OD) δ 7.28 (td, J=8.0, 6.2 Hz, 1H), 7.22-7.17 (m, 1H), 7.16-7.09 (m, 1H), 6.96-6.85 (m, 1H), 3.99-3.93 (m, 2H), 3.71 (d, J=12.0 Hz, 1H), 3.56 (dd, J=11.9, 9.5 Hz, 1H), 1.52 (tt, J=9.1, 6.1 Hz, 1H), 1.10 (dd, J=8.7, 5.1 Hz, 1H), 0.85 (t, J=5.5 Hz, 1H); $^{13}$C NMR (126 MHz, CD$_3$OD) δ 164.10 (d, $J_{CF}$=243.6 Hz), 148.96 (d, $J_{CF}$=7.5 Hz), 130.74 (d, $J_{CF}$=8.4 Hz), 125.61 (d, $J_{CF}$=2.7 Hz), 116.77 (d, $J_{CF}$=21.6 Hz), 113.93 (d, $J_{CF}$=21.3 Hz), 67.16, 63.31, 33.04, 28.09, 17.44.

HPLC Method for Monitoring Process Step B:

Equipment:
- HPLC column: Waters SunFire C18, 3.5 um 3×150 mm, Waters catalog no. 186002544.
- Solvent Delivery System: Agilent 1100 HPLC quaternary pump, low pressure mixing, with an in-line degasser, or equivalent.
- Autosampler: Agilent 1100 autosampler, variable loop, 0.1 to 100 μL range, or equivalent.
- Detector: Agilent 1100 Diode Array Detector or equivalent.
- Chromatographic Agilent ChemStation software version A.09.03 or
- Software: higher for HPLC, Waters Empower 2 Build 2154, or equivalent.
- Volumetric Glassware: Class A.
- Balance: Analytical balance, capable of weighing ±0.1 mg.

Reagents:
- Water: HPLC grade, (Baker cat no. 4218-03) or equivalent
- Acetonitrile: HPLC grade, (Baker cat no. 9017-03) or equivalent.
- Trifluoroacetic acid (TFA): Spectrophotometric grade, Aldrich (catalog no. 302131) or equivalent.

Mobile Phase:
- Solvent A: Add 1000 mL of water to an appropriate flask. Add 1.0 mL of trifluouroacetic acid and mix. Degas in-line during use.
- Solvent B: Add 1000 mL of acetonitrile to an appropriate flask. Add 1.0 mL of trifluouroacetic acid and mix. Degas in-line during use.

HPLC Parameters

Chromatographic Parameters

| HPLC column: | Waters SunFire C18, 3.5 um 3 × 150 mm, Waters catalog no. 186002544. |
|---|---|
| Temperature: | 40° C. |
| Flow rate: | 0.5 mL/min Flow rate may be adjusted ± 0.1 mL/min to obtain specified retention times. |

| | Time, min | %-Solvent A | %-Solvent B |
|---|---|---|---|
| Gradient: | Initial | 95 | 5 |
| | 5 | 70 | 30 |
| | 9 | 60 | 40 |
| | 17 | 0 | 100 |
| | 20 | 0 | 100 |
| | 20.1 | 95 | 5 |
| | 30 | 95 | 5 |

| Injection volume: | 4 μL |
|---|---|
| Detection: | 220 nm UV |
| Data acquisition time: | 20 min |
| Run time: | 30 min |

C. Preparation of Acetates of Formula III

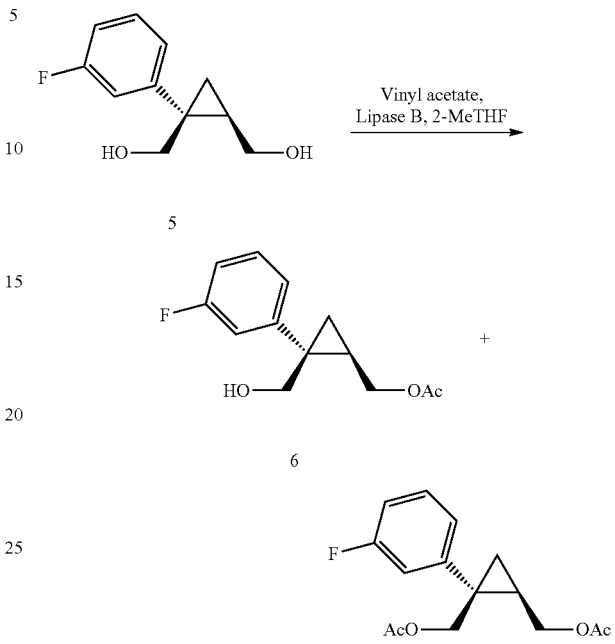

(((1R,2S)-2-(3-fluorophenyl)-2-(hydroxymethyl)cyclopropyl)methyl acetate (6)

((1S,2R)-1-(3-fluorophenyl)cyclopropane-1,2-diyl)dimethanol (5, 7.89 g, 0.040 mol, 1.0 equiv.) was dissolved in 2-methyl-THF (23.68 mL), under nitrogen. Lipase acrylic resin (Candida Antarctica Lipase B, Sigma-Aldrich, Saint Louis, Mo.) (417.5 mg, 5.0 wt %) was added. Vinyl acetate (5.56 mL, 0.060 mol, 1.5 equiv.) was added, and the reaction mixture was stirred at 20-25° C. while monitoring the ratio of mono-acetate and diacetate (8-9 h) by HPLC and TLC (EtOAc/Heptane=1/1). Upon reaction completion, the lipase was removed by filtration and rinsed with 2-methyl-THF (71.04 mL). The filtrate and the rinse were combined and washed with 15% NaCl aq. solution (27.63 mL) followed by sat. aqueous NaCl solution (23.68 mL). The solvent was removed under reduced pressure then azeotroped with 2-methyl-THF until KF is less than 1500 ppm to afford the title compound, ((1R,2S)-2-(3-fluorophenyl)-2-(hydroxymethyl)cyclopropyl)methyl acetate, 6 (9.59 g).

((1R,2S)-2-(3-fluorophenyl)-2-(hydroxymethyl)cyclopropyl)methyl acetate: $^1$H NMR (500 MHz, CD$_3$OD) δ 7.28 (tt, J=19.4, 9.7 Hz, 1H), 7.18-7.14 (m, 1H), 7.12-7.04 (m, 1H), 6.96-6.87 (m, 1H), 4.36 (dd, J=11.9, 7.2 Hz, 1H), 4.25 (dd, J=11.9, 8.3 Hz, 1H), 3.85 (d, J=11.9 Hz, 1H), 3.77 (d, J=11.9 Hz, 1H), 2.09 (s, 3H), 1.58-1.49 (m, 1H), 1.15 (dd, J=8.8, 5.1 Hz, 1H), 0.95-0.90 (m, 1H); $^{13}$C NMR (126 MHz, CD$_3$OD) δ 173.03, 164.10 (d, $J_{CF}$=243.8 Hz), 148.31 (d, $J_{CF}$=7.4 Hz), 130.86 (d, $J_{CF}$=8.4 Hz), 125.78 (d, $J_{CF}$=2.8 Hz), 116.90 (d, $J_{CF}$=21.4 Hz), 114.16 (d, $J_{CF}$=21.3 Hz), 66.46, 65.77, 33.39, 24.73, 20.92, 16.79.

HPLC Method for Monitoring Process Step B:
Equipment, Reagents, and Mobile Phase:
  Equipment:
    HPLC column: Waters SunFire C18, 3.5 um 3×150 mm, Waters catalog no. 186002544.
    Solvent Delivery System Agilent 1100 HPLC quaternary pump, low pressure mixing, with an in-line degasser, or equivalent.
    Autosampler: Agilent 1100 autosampler, variable loop, 0.1 to 100 μL range, or equivalent.
    Detector: Agilent 1100 Diode Array Detector or equivalent.
    Chromatographic Agilent ChemStation software version A.09.03 or
  Software: higher for HPLC, Waters Empower 2 Build 2154, or equivalent.
  Volumetric Glassware: Class A.
  Balance: Analytical balance, capable of weighing±0.1 mg.
  Reagents:
    Water: HPLC grade, (Baker cat no, 4218-03) or equivalent
    Acetonitrile: HPLC grade, (Baker cat no. 9017-03) or equivalent.
    Trifluoroacetic acid (TFA): Spectrophotometric grade, Aldrich (catalog no. 302131) or equivalent.
  Mobile Phase:
    Solvent A: Add 1000 mL of water to an appropriate flask. Add 1.0 mL of trifluouroacetic acid and mix. Degas in-line during use.
    Solvent B: Add 1000 mL of acetonitrile to an appropriate flask. Add 1.0 mL of trifluouroacetic acid and mix. Degas in-line during use.
HPLC Parameters:

| HPLC column: | Waters SunFire C18, 3.5 um 3 × 150 mm, Waters catalog no. 186002544. |  |  |
|---|---|---|---|
| Temperature: | 40° C. | | |
| Flow rate: | 0.5 mL/min. Flow rate may be adjusted ± 0.1 mL/min to obtain specified retention times. | | |
| | Time, min, | %-Solvent A | %-Solvent B |
| Gradient: | Initial | 95 | 5 |
| | 5 | 70 | 30 |
| | 9 | 60 | 40 |
| | 17 | 0 | 100 |
| | 20 | 0 | 100 |
| | 20.1 | 95 | 5 |
| | 30 | 95 | 5 |
| Injection volume: | 4 μL | | |
| Detection: | 220 nm UV | | |
| Data acquisition time: | 20 min | | |
| Run time: | 30 min | | |

D. Preparation of Compounds of Formula IV

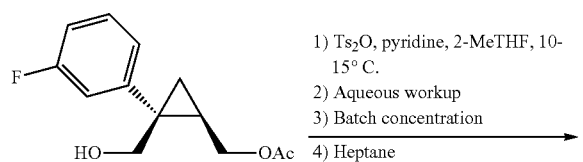

1) Ts₂O, pyridine, 2-MeTHF, 10-15° C.
2) Aqueous workup
3) Batch concentration
4) Heptane
5) Cool to 0° C.
6) Filter and wash

6

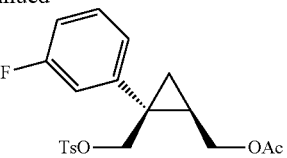

8

(((1R,2S)-2-(3-fluorophenyl)-2-((tosyloxy)methyl)cyclopropyl)methyl acetate (8)

((1R,2S)-2-(3-fluorophenyl)-2-(hydroxymethyl)cyclopropyl)methyl acetate (6, 9.59 g, 0.040 mol, 1.0 equiv.) was dissolved in 2-methyl-THF (95.9 mL), under nitrogen. The solution was cooled to 10-15° C., and pyridine (11.4 mL, 0.141 mol, 3.5 equiv.) was added to the reaction mixture while maintaining the internal temperature below 15° C., p-Toluenesulfonic acid anhydride (15.76 g, 0.048 mol, 1.2 equiv.) solid was added to the reaction mixture in portions while maintaining the internal temperature below 15° C. The reaction was stirred at 10-15° C. for at least 1 hour while being monitored by HPLC and TLC (EtOAc/Heptane=1/1). Upon completion of the reaction, the reaction mixture was quenched with water (38.4 mL) while maintaining the internal temperature below 25° C. The organic layer was washed twice with 1 N HCl (38.0 mL each wash) to pH 1-2 (second aqueous wash), and then was washed with saturated aqueous NaHCO₃ solution (33.6 mL) to pH≥7 followed by sat. aqueous NaCl solution (23.98 mL). The organic layer was separated and concentrated under reduced pressure to approximately 24.0 mL. n-Heptane (86.3 mL) was added slowly with agitation. The suspension was stirred for at least 30 min at 20-22° C. and then stirred for at least 1 h at 0-5° C. The suspension was filtered and the cake was washed at least two times with n-heptane (14.4 mL used for each wash). The cake was dried under nitrogen and/or vacuum to provide the title compound (((1R,2S)-2-(3-fluorophenyl)-2-((tosyloxy)methyl)cyclopropyl)methyl acetate, (8, 11.05 g, 89.3% ee) as an off white to tan solid.

((1R,2S)-2-(3-fluorophenyl)-2-((tosyloxy)methyl)cyclopropyl)methyl acetate: $^1$H NMR (500 MHz, CD₃OD) δ 7.55 (d, J=8.3 Hz, 2H), 7.32-7.27 (m, 2H), 7.23 (td, J=8.0, 6.1 Hz, 1H), 7.02 (dd, J=7.7, 0.9 Hz, 1H), 6.95-6.90 (m, 1H), 6.90-6.84 (m, 1H), 4.36 (d, J=10, 9 Hz, 1H), 4.32 (dd, J=12.1, 6.3 Hz, 1H), 4.17 (d, J=10.9 Hz, 1H), 4.08 (dd, J=12.1, 9.1 Hz, 1H), 2.42 (s, 3H), 2.09 (s, 3H), 1.68 (tt, J=9.0, 6.3 Hz, 1H), 1.19 (dd, J=8.9, 5.5 Hz, 1H), 1.00 (t, J=5.8 Hz, 1H); $^{13}$C NMR (126 MHz, CD₃OD) δ 171.38, 162.58 (d, $J_{CF}$=244.6 Hz), 144.92, 144.51 (d, $J_{CF}$=7.4 Hz), 132.52, 129.73 (d, $J_{CF}$=8.5 Hz), 129.51, 127.36, 124.50 (d, $J_{CF}$=2.9 Hz), 115.47 (d, $J_{CF}$=21.8 Hz), 113.45 (d, $J_{CF}$=21.3 Hz), 74.17, 63.50, 28.94, 23.49, 20.11, 19.49, 15.67.

HRMS Calculated for $C_{20}H_{21}FO_5SNa$ $[M+Na]^+$ 415.0991. found 415.0973.

HPLC Method for Monitoring Process Step D:
Mobile Phase:
  Solvent A: 1000 mL of water and 1.0 mL of trifluoroacetic acid
  Solvent B: 1000 mL of acetonitrile and 1.0 mL of trifluoroacetic acid

41

HPLC Parameters:

| HPLC column: | Waters SunFire C18, 3.5 um 3 × 150 mm, Waters catalog no. 186002544. |
| --- | --- |
| Temperature: | 40° C. |
| Flow rate: | 0.5 mL/min. Flow rate may be adjusted ± 0.1 mL/min to obtain specified retention times. |

| | Time, min | %-Solvent A | %-Solvent B |
| --- | --- | --- | --- |
| Gradient: | Initial | 95 | 5 |
| | 5 | 70 | 30 |
| | 9 | 60 | 40 |
| | 17 | 0 | 100 |
| | 20 | 0 | 100 |
| | 20.1 | 95 | 5 |
| | 30 | 95 | 5 |

| Injection volume: | 2 μL |
| --- | --- |
| Detection: | 215 nm UV |
| Data acquisition time: | 20 min |
| Run time: | 30 min |

Chiral HPLC Assay for 8
TM-1257: Chiral HPLC Assay for 8
Equipment, Reagents, and Mobile Phase:
Equipment:

| HPLC column: | AD-H 4.6 × 250 mm 5 μm, Chiral Tech catalog no. 19325. |
| --- | --- |
| Solvent Delivery System: | Agilent 1100 HPLC quaternary pump, low pressure mixing with an in-line degasser, or equivalent. |
| Autosampler: | Agilent 1100 autosampler, 0.1 to 100 μL range, or equivalent. |
| Detector: | Agilent 1100 Diode Array Detector or equivalent. |
| Chromatographic Software: | Agilent ChemStation software version A.09.03 or higher for HPLC, Waters Empower 2 Build 2154, or equivalent. |
| Volumetric Glassware: | Class A. |
| Volumetric pipette: | Class A. |
| Balance: | Analytical balance, capable of weighing ± 0.1 mg. |

Reagents:

| Hexanes: | HPLC grade, EMD (catalog no. HX0296-1) or equivalent. |
| --- | --- |
| 2-Propanol: | HPLC grade, J. T. Baker (catalog no. 9095-03) or equivalent. |

Mobile Phase:
Mobile phase A:
Using appropriate graduated cylinders, add 900 mL of hexanes and 100 mL of 2-propanol to an appropriate flask. Mix well and degas in line during use.
HPLC Parameters:
Chromatographic Parameters:

| HPLC column: | AD-H, 250 × 4.6 mm, 5 μm, Chiral Tech Catalog no. 19325, or equivalent. |
| --- | --- |
| Temperature: | 25° C. |
| Flow rate: | 1.0 mL/min. Flow rate may be adjusted to obtain specified retention times. |
| Isocratic: | Solvent A |
| Injection volume: | 5.0 μL |
| Detection: | UV detector 217 nm |
| Acquisition time: | 20 min |
| Re-equilibration time: | Not Applicable |
| Total run time: | 20 min |

42

Calculations:
%-Enantiomeric Excess Calculation:
Calculate the %-enantiomeric excess (%-ee) for 8 using the appropriate peak areas obtained from each sample analysis and the following equation:

$$\% \ ee = \frac{(A_8 - A_9)(100\%)}{(A_8 + A_9)}$$

$A_8$ = Average Peak area of 8 from each sample solution $A_9$ = Average Peak area of 9 from each sample solution Note: Compound 9 is the enantiomer of compound 8.
An enantiomeric excess was calculated at 89.3% for compound 8.

E. Preparation of Compounds of Formula V

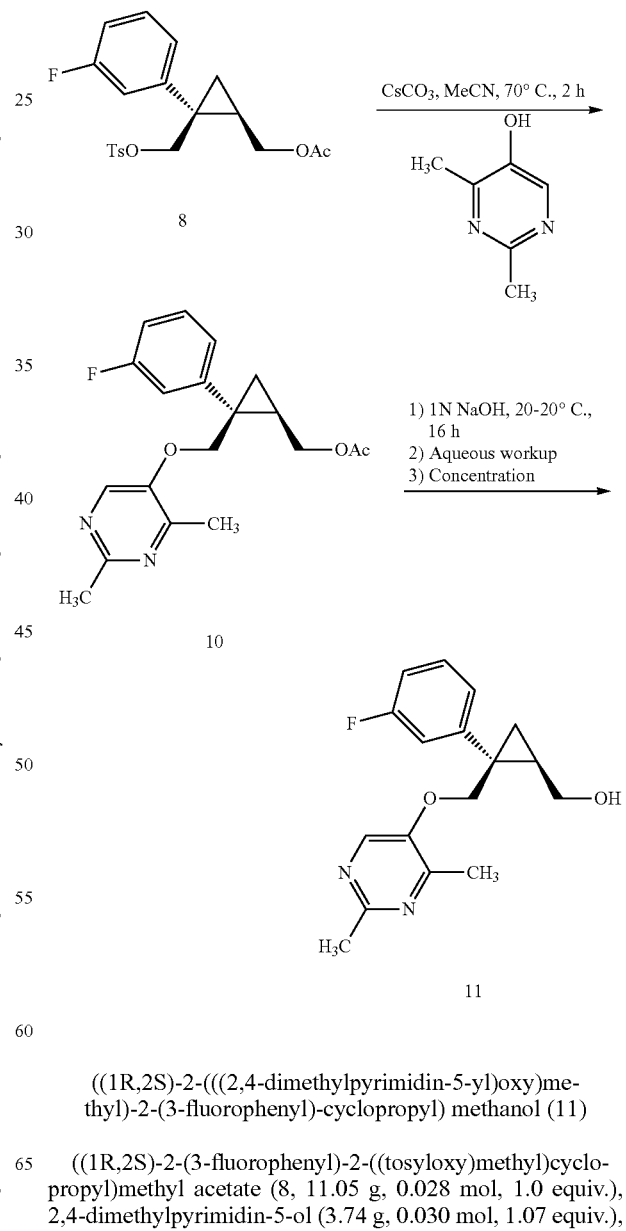

((1R,2S)-2-(((2,4-dimethylpyrimidin-5-yl)oxy)methyl)-2-(3-fluorophenyl)-cyclopropyl) methanol (11)

((1R,2S)-2-(3-fluorophenyl)-2-((tosyloxy)methyl)cyclopropyl)methyl acetate (8, 11.05 g, 0.028 mol, 1.0 equiv.), 2,4-dimethylpyrimidin-5-ol (3.74 g, 0.030 mol, 1.07 equiv.), and cesium carbonate (22.94 g, 1.8 equiv.) were dissolved in ACN (110.5 mL), under nitrogen. The solution was stirred vigorously and heated to 65-70° C. for 2-3 hours. The reaction was monitored by HPLC and TLC (EtOAc/Heptane=1/1). Once complete, aqueous 1 N NaOH solution (71.82 mL) was added to the reaction mixture. The reaction mixture was stirred at 20-25° C. for 10-16 h, and was monitored by HPLC and TLC (EtOAc/Heptane=1/1). Once the hydrolysis reaction was complete, the reaction mixture was diluted with MTBE (110.50 mL) and stirred for at least 15 min. The aqueous layer was back extracted once with MTBE (55.25 mL). The organic layers were combined and washed once with saturated aqueous NaCl solution (33.15 mL), The solvent was removed under reduced pressure to afford the title compound; ((1R,2S)-2-(((2,4-dimethylpyrimidin-5-yl)oxy)methyl)-2-(3-fluorophenyl)cyclopropyl)methanol: (11, 8.51 g).

((1R,2S)-2-(((2,4-dimethylpyrimidin-5-yl)oxy)methyl)-2-(3-fluorophenyl)-cyclopropyl)methanol: $^1$H NMR (500 MHz, DMSO-$d_6$) δ 8.21 (s, 1H), 7.33 (td, J=8.0, 6.5 Hz, 1H), 7.20 (d, J=7, 9 Hz, 1H), 7.19-7.14 (m, 1H), 7.01 (ddd, J=8.3, 2.6, 1.2 Hz, 1H), 4.63 (t, J=5.4 Hz, 1H), 4.36 (dd, J=22.5, 10.5 Hz, 2H), 3.72-3.61 (m, 2H), 2.45 (s, 3H), 2.22 (s, 3H), 1.51-1.43 (m, 1H), 1.23 (dd, J=8.9, 5.0 Hz, 1H), 1.01 (dd, J=6.0, 5.3 Hz, 1H). $^{13}$C NMR (126 MHz, DMSO-$d_6$) δ 162.48 (d, $J_{CF}$=243.0 Hz), 158.91, 156.26, 149.51, 147.47 (d, $J_{CF}$=7.5 Hz), 139.85, 130.35 (d, $J_{CF}$=8.5 Hz), 124.72 (d, $J_{CF}$=2.5 Hz), 115.54 (d, $J_{CF}$=21.3 Hz), 113.43 (d, F=20.9 Hz), 72.73, 60.70, 29.23, 28.64, 24.94, 18.77, 17.06.

HRMS Calculated for $C_{17}H_{20}FN_2O_2$ [M+H]$^+$ 303.1590. found 303.1517.

HPLC Method for Monitoring Process Step E:
Sample Preparation:
Combine reaction mixture (5 μL) with 1 mL acetonitrile, mix and inject.
Summary of Chromatography Conditions:

| HPLC column: | Waters SunFire C18, 3.5 um 3 × 150 mm, Waters catalog no. 186002544. |
| --- | --- |
| Temperature: | 40° C. |
| Flow rate: | 0.5 mL/min. Flow rate may be adjusted ± 0.1 mL/min to obtain specified retention times. |
| Mobile Phase A | 1000 mL water and 1 mL trifluoroacetic acid |
| Mobile Phase B | 1000 mL acetonitrile and 1 mL trifluoroacetic acid |

| | Time, min | %-Solvent A | %-Solvent B |
| --- | --- | --- | --- |
| Gradient: | Initial | 95 | 5 |
| | 5 | 70 | 30 |
| | 9 | 60 | 40 |
| | 17 | 0 | 100 |
| | 20 | 0 | 100 |
| | 20.1 | 95 | 5 |
| | 30 | 95 | 5 |

| Injection volume: | 3 μL |
| --- | --- |
| Detection: | 215 nm UV |
| Data acquisition time: | 20 min |
| Run time: | 30 min |
| 18 Retention time: | 3.0 min ± 10% |
| 11 Retention time: | 10.2 min ± 10% |
| 10 Retention time: | 13.5 min ± 10% |
| 8 Retention time: | 17.2 min ± 10% |

F. Preparation of Compounds of Formula VII

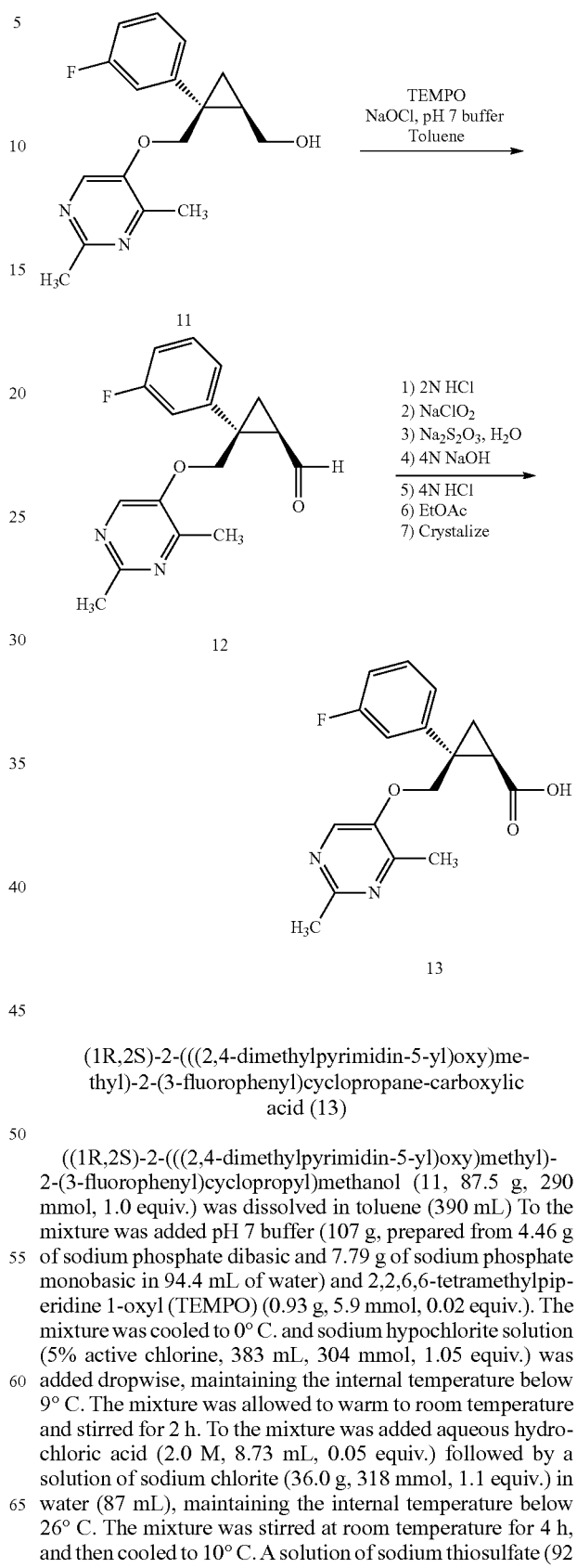

(1R,2S)-2-(((2,4-dimethylpyrimidin-5-yl)oxy)methyl)-2-(3-fluorophenyl)cyclopropane-carboxylic acid (13)

((1R,2S)-2-(((2,4-dimethylpyrimidin-5-yl)oxy)methyl)-2-(3-fluorophenyl)cyclopropyl)methanol (11, 87.5 g, 290 mmol, 1.0 equiv.) was dissolved in toluene (390 mL) To the mixture was added pH 7 buffer (107 g, prepared from 4.46 g of sodium phosphate dibasic and 7.79 g of sodium phosphate monobasic in 94.4 mL of water) and 2,2,6,6-tetramethylpiperidine 1-oxyl (TEMPO) (0.93 g, 5.9 mmol, 0.02 equiv.). The mixture was cooled to 0° C. and sodium hypochlorite solution (5% active chlorine, 383 mL, 304 mmol, 1.05 equiv.) was added dropwise, maintaining the internal temperature below 9° C. The mixture was allowed to warm to room temperature and stirred for 2 h. To the mixture was added aqueous hydrochloric acid (2.0 M, 8.73 mL, 0.05 equiv.) followed by a solution of sodium chlorite (36.0 g, 318 mmol, 1.1 equiv.) in water (87 mL), maintaining the internal temperature below 26° C. The mixture was stirred at room temperature for 4 h, and then cooled to 10° C. A solution of sodium thiosulfate (92 g, 579 mmol, 2.0 equiv.) in water (177 mL) was added, maintaining the internal temperature below 20° C. The mixture was stirred for 20 min, and then aqueous sodium hydroxide solution (4 N, 87 mL, 348 mmol, 1.2 equiv.) was added to achieve ca. pH=13. The mixture was heated to 80° C. for 4 hours, then cooled to room temperature. Stirring was halted and the phases allowed to split. The lower aqueous phase was collected and the upper organic phase was washed once with 4 N sodium hydroxide solution (17 mL). The combined aqueous phases were acidified with aqueous hydrochloric acid solution (4 N, 17 mL) to pH=4 and extracted with ethyl acetate (2×470 mL). The combined organic phases were washed with ca. 20% aqueous NaCl solution (175 mL) The organic phases were concentrated by rotary evaporation to yield 96.84 g of crude oil. A portion (74 g) of this crude oil was dissolved in acetonitrile (400 mL) and concentrated to dryness by rotary evaporation. Another portion of acetonitrile (400 mL) was added and the mixture was again concentrated to dryness. To the residue was added acetonitrile (370 mL). The mixture was heated to 65° C. resulting in a clear solution. The mixture was cooled to room temperature, then to 0° C. and held at this temperature for 6 h. The mixture was filtered and the wet cake was washed with acetonitrile (2×74 mL). The cake was dried under vacuum with a nitrogen sweep, then in a vacuum oven at 20 torr and 40° C. to afford (1R,2S)-2-(((2,4-dimethylpyrimidin-5-yl)oxy)methyl)-2-(3-fluorophenyl)cyclopropanecarboxylic acid (13, 56.9 g, 80% yield) as an off-white crystalline solid.

(1R,2S)-2-(((2,4-dimethylpyrimidin-5-yl)oxy)methyl)-2-(3-fluorophenyl)-cyclopropanecarboxylic acid: $^1$H NMR (500 MHz, DMSO-$d_6$) δ 12.47 (s, 1H), 8.17 (s, 1H), 7.39 (td, J=8.0, 6.4 Hz, 1H), 7.29 (d, J=7.9 Hz, 1H), 7.27-7.22 (m, 1H), 7.10 (td, J=8.3, 2.1 Hz, 1H), 4.63 (d, J=10.2 Hz, 1H), 4.30 (d, J=10.2 Hz, 1H), 2.46 (s, 3H), 2.26 (s, 3H), 2.13 (dd, J=7.7, 6.6 Hz, 1H), 1.63-1.54 (m, 2H); $^{13}$C NMR (126 MHz, DMSO-$d_6$) δ 172.65, 162.48 (d, $J_{CF}$=243.6 Hz), 159.08, 156.24, 149.45, 145.15 (d, $J_{CF}$=7.5 Hz), 139.60, 130.71 (d, $J_{CF}$=8.5 Hz), 124.79 (d, $J_{CF}$=2.6 Hz), 115.60 (d, $J_{CF}$=21.8 Hz), 114.32 (d, $J_{CF}$=20.8 Hz), 71.15, 33.92 (d, $J_{CF}$=2.0 Hz), 26.46, 24.96, 19.72, 18.70.

HRMS Calculated for $C_{17}H_{18}FN_2O_3$ [M+H]$^+$ 317.1301. found 317.1298.

Sample Preparation:
Transfer 10 µL of reaction mixture to an HPLC vial containing 1 mL diluting solution, and mix by vortexing. Transfer 100 µL of this solution to an HPLC vial containing 1 mL diluting solution, and mix by vortexing. This is the sample solution.

Summary of Chromatography Conditions:

| HPLC column: | Waters SunFire C18, 3.5 um 3 × 150 mm, Waters catalog no. 186002544. |
|---|---|
| Temperature: | 40° C. |
| Flow rate: | 0.5 mL/min. Flow rate may be adjusted ± 0.1 mL/min to obtain specified retention times. |
| Mobile Phase A | 1000 mL water and 1 mL trifluoroacetic acid |
| Mobile Phase B | 1000 mL acetonitrile and 1 mL trifluoroacetic acid |

| | Time, min | %-Solvent A | %-Solvent B |
|---|---|---|---|
| Gradient: | Initial | 95 | 5 |
| | 5 | 70 | 30 |
| | 9 | 60 | 40 |
| | 17 | 0 | 100 |
| | 20 | 0 | 100 |
| | 20.1 | 95 | 5 |
| | 30 | 95 | 5 |

| Injection volume: | 3 µL |
|---|---|
| Detection: | 220 nm UV |
| Data acquisition time: | 20 min |
| Run time: | 30 min |
| 11 Retention time: | 10.2 min ± 10% |
| 12 Retention time: | 11.7 min ± 10% |
| 13 Retention time: | 10.6 min ± 10% |

G. Preparation of Compounds of Formula IX

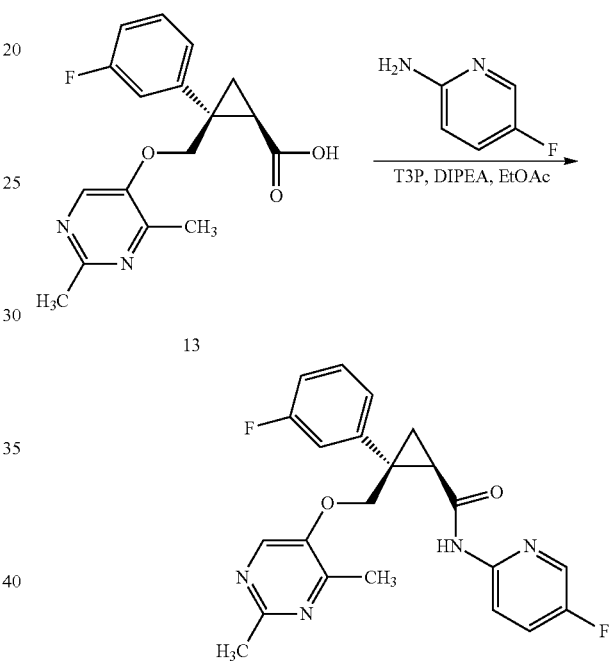

(1R,2S)-2-(((2,4-dimethylpyrimidin-5-yl)oxy)methyl)-2-(3-fluorophenyl)-N-(5-fluoropyridin-2-yl)cyclopropanecarboxamide (14)

(1R,2S)-2-(((2,4-dimethylpyrimidin-5-yl)oxy)methyl)-2-(3-fluorophenyl)-cyclopropanecarboxylic acid (13, 12.80 g, 0.040 mol, 1.0 equiv.), and 2-amino-5-fluoropyridine (4.76 g, 0.0425 mol, 1.05 equiv.) were dissolved in ethyl acetate (102.4 mL), under nitrogen. The solution was cooled to 0-5° C., and N,N-diisopropylethylamine (14.10 mL, 0.081 mol, 2.0 equiv.) was added to the reaction mixture while maintaining the internal temperature at 0-15° C. The reaction mixture was stirred at 0-10° C. for 20-30 minutes. n-Propylphosphonic anhydride (T3P; 50% w/w solution in ethyl acetate, 36.1 g, 1.4 equiv.) was added to the reaction mixture while maintaining the internal temperature at 0-15° C., The reaction was stirred at 20-25° C. for at least 20-24 hour and monitored by HPLC and TLC (EtOAc/Heptane=1/1), Upon completion of the reaction, the reaction mixture was cooled to 0-5° C. and then was quenched with water (64.0 mL) while maintaining the internal temperature below 10-15° C. The aqueous layer was back extracted once with MTBE (76.8 mL). The organic layers were combined and washed once with saturated aqueous $NaHCO_3$ solution (38.4 mL) and once with water (38.4 mL). The organic layer was polish filtered and the filter rinsed with MTBE (12.8 mL). The organic layer was then concentrated under reduced pressure to a minimum stirrable volume. Ethyl acetate (60.8 mL) was added to the reaction mixture and the mixture was heated to no more than 50° C. to achieve a clear solution. n-Heptane (86.3 mL) was added slowly with agitation. The reaction mixture was cooled to 20-25° C., and the suspension was stirred for at least 1 h at 20-25° C. and then stirred at least for 1 h at 0-5° C. The suspension was filtered and the cake was washed two times with 5:1 heptane/ethyl acetate (2× 12.8 mL). The cake was dried under nitrogen and/or vacuum to provide the title compound, (1R,2S)-2-(((2,4-dimethylpyrimidin-5-yl)oxy)methyl)-2-(3-fluorophenyl)-N-(5-fluoropyridin-2-yl)cyclopropanecarboxamide, (14, 12.54 g, >99% ee) as a white to off white solid.

(1R,2S)-2-(((2,4-dimethylpyrimidin-5-yl)oxy)methyl)-2-(3-fluorophenyl)-N-(5-fluoropyridin-2-yl)cyclopropanecarboxamide: $^1$H NMR (500 MHz, DMSO-$d_6$) δ 11.19 (s, 8.31 (d, J=3.0 Hz, 1H), 8.12 (s, 1H), 7.94-7.85 (m, 1H), 7.62 (tt, J=8.7, 3.1 Hz, 1H), 7.44 (dd, J=10.6, 1.5 Hz, 1H), 7.41-7.40 (m, 1H), 7.39 (s, 1H), 7.14-7.06 (m, 1H), 4.67 (d, J=10.2 Hz, 1H), 4.29 (t, J=9.9 Hz, 1H), 2.63 (t, J=7.0 Hz, 1H), 2.38 (s, 3H), 2.03 (s, 3H), 1.76-1.64 (m, 1H), 1.49 (dd, J=8.0, 4.8 Hz, 1H); $^{13}$C NMR (125 MHz, DMSO-$d_6$) δ 168.68, 161.98 (d, $J_{CF}$=242.3 Hz), 158.46, 155.15, 155.38 (d, $J_{CF}$=247.9 Hz), 148.90, 148.51, 145.00 (d, $J_{CF}$=7.7 Hz), 139.37, 135.15 (d, $J_{CF}$=24.9 Hz), 130.06 (d, $J_{CF}$=8.4 Hz), 125.05 (d, $J_{CF}$=19.5 Hz), 124.70 (d, $J_{CF}$=2.6 Hz), 115.71 (d, $J_{CF}$=21.7 Hz), 114.20 (d, $J_{CF}$=4.1 Hz), 113.70 (d, $J_{CF}$ 20.9 Hz), 70.80, 34.09 (d, $J_{CF}$=1.9 Hz), 26.90, 24.38, 18.37, 17.78.

HRMS Calculated for $C_{22}H_{21}F_2N_4O_2$ $[M+H]^+$ 411.1627. found 411.1632.

Sample Preparation:

Transfer 500 μL of reaction mixture to an HPLC vial containing 500 μL acetonitrile, and mix by vortexing.

Summary of Chromatography Conditions:

| HPLC column: | Waters SunFire C18, 3.5 um 3 × 150 mm, Waters catalog no. 186002544. |
|---|---|
| Temperature: | 40° C. |
| Flow rate: | 0.5 mL/min Flow rate may be adjusted ± 0.1 mL/min to obtainspecified retention times. |
| Mobile Phase A | 1000 mL water and 1 mL trifluoroacetic acid |
| Mobile Phase B | 1000 mL acetonitrile and 1 mL trifluoroacetic acid |

| | Time, min | %-Solvent A | %-Solvent B |
|---|---|---|---|
| Gradient: | Initial | 95 | 5 |
| | 5 | 70 | 30 |
| | 9 | 60 | 40 |
| | 17 | 0 | 100 |
| | 20 | 0 | 100 |
| | 20.1 | 95 | 5 |
| | 30 | 95 | 5 |

| Injection volume: | 2 μL | |
|---|---|---|
| Detection: | 220 nm UV | |
| Data acquisition time: | 20 min | |
| Run time: | 30 min | |
| Retention times: | 13 | 10.6 min ± 10% |
| | 14 | 13.2 min ± 10% |
| | Ethyl acetate | 7.5 min ± 10% |

Chiral HPLC Assay for (1R,2S)-2-(((2,4-dimethylpyrimidin-5-yl)oxy)methyl)-2-(3-fluorophenyl)-N-(5-fluoropyridin-2-yl)cyclopropanecarboxamide (14)

TM-1186: Chiral HPLC Assay for Compound 14
Equipment, Reagents, and Mobile Phase:
Equipment:

| HPLC column: | CHIRALPAK AD-H, 250 × 4.6 mm, 5 μm, Chiral Technologies catalog no. 19325, or equivalent. |
|---|---|
| Solvent Delivery System: | Agilent 1100 HPLC quaternary pump, low pressure mixing with an in-line degasser, or equivalent. |
| Autosampler: | Agilent 1100 autosampler, 0.1 to 100 μL range, or equivalent. |
| Detector: | Agilent 1100 variable wavelength detector or equivalent. |
| Chromatographic Software: | Agilent ChemStation software version A.09.03 or higher for HPLC, Waters Empower 2 Build 2154, or equivalent. |
| Volumetric Glassware: | Class A. |
| Volumetric pipette: | Class A. |
| Balance: | Analytical balance, capable of weighing ± 0.1 mg. |

Reagents:

| Heptane: | HPLC grade, EMD (catalog no. HX0078-1) or equivalent. |
|---|---|
| 2-Propanol: | HPLC grade, EMD (catalog no. PX1838-1) or equivalent. |

Mobile Phase:
  Mobile phase A: Add 1000 mL of heptane to an appropriate flask. Mix well and degas in line during use.
  Mobile phase B: Add 1000 mL of 2-propanol to an appropriate flask. Mix well and degas in line during use.
HPLC Parameters:
Chromatographic Parameters:

| HPLC column: | CHIRALPAK AD-H, 250 × 4.6 mm, 5 μm, Chiral Technologies catalog no. 19325, or equivalent. |
|---|---|
| Temperature: | 35° C. |
| Flow rate*: | 1.0 mL/min. Flow rate may be adjusted to obtain specified retention times. |
| Gradient: | Isocratic, 80/20 (vol/vol) mobile phase A/mobile phase B |
| Injection volume: | 5.0 μL |
| Detection: | UV detector 282 nm |
| Acquisition time: | 15 min |
| Re-equilibration time: | N/A |
| Total run time: | 15 min |

Calculations:
%-Enantiomeric Excess Calculation:
  Calculate the %-enantiomeric excess (%-ee) for 14 using the appropriate peak areas obtained from each sample analysis and the following equation:

$$\% \ ee = \frac{(A_{14} - A_{15})(100\%)}{(A_{14} + A_{15})}$$

$A_{14}$ = Average Peak area of 14 from each sample solution $A_{15}$ = Average Peak area of 15 from each sample solution Note: The enantiomer of compound 14 is compound 15. An enantiomeric excess was calculated at >99% for compound 14.

Alternate Procedure for Preparation of Compounds of Formula IX (1R,2S)-2-(((2,4-dimethylpyrimidin-5-yl)oxy)methyl)-2-(3-fluorophenyl)-N-(5-fluoropyridin-2-yl)cyclopropanecarboxamide (14)

(1R,2S)-2-(((2,4-dimethylpyrimidin-5-yl)oxy)methyl)-2-(3-fluorophenyl)cyclopropane-carboxylic acid (13, 12.80 g, 0.040 mol, 1.0 equiv.), 2-amino-5-fluoropyridine (4.76 g, 0.0425 mol, 1.05 equiv.), and N,N,N',N'-tetramethyl-O-(7-azabenzotriazol-1-yl)uronium hexafluorophosphate (HATU; 16.16 g, 0.0425 mol, 1.05 equiv.) were dissolved in DMF (64.0 mL), under nitrogen. The solution was cooled to 0-5° C., and N,N-diisopropylethylamine (14.10 mL, 0.081 mol, 2.0 equiv.) was added to the reaction mixture while maintaining the internal temperature below 10° C. The reaction was stirred at 20-25° C. for at least 20-24 hour and monitored by HPLC and TLC (EtOAc/Heptane=1/1). If (1R,2S)-2-(((2,4-dimethylpyrimidin-5-yl)oxy)methyl)-2-(3-fluorophenyl)cyclopropane-carboxylic acid was >2%, additional N,N,N',N'-tetramethyl-O-(7-azabenzotriazol-1-yl)uronium hexafluorophosphate was added (based on the conversion) at 20-25° C., and then N,N-diisopropylethylamine (based on the conversion) was added to the reaction mixture while maintaining the internal temperature below 10° C. If (1R,2S)-2-(((2,4-dimethylpyrimidin-5-yl)oxy)methyl)-2-(3-fluorophenyl)cyclopropane-carboxylic acid was ≤2%, but the conversion to the titled compound from the intermediate was <97%, additional 2-amino-5-fluoropyridine (based on the conversion) was added to the reaction mixture at 20-25° C. Upon completion of the reaction, the reaction mixture was diluted with MTBE (51.2 mL) and was cooled to 0-5° C. It was quenched with water (64.0 mL) while maintaining the internal temperature below 10-15° C. The reaction mixture was warmed up to 20-25° C., and MTBE (76.8 mL) was added. The aqueous layer was back extracted once with MTBE (128.0 mL) and once with toluene (102.4 mL). The organic layers were combined and washed once with saturated aqueous NaHCO₃ solution (38.4 mL) and with 18% aq. NaCl solution (2×32.0 mL). The HATU by product in the organic layer was analyzed: if it was >0.2%, additional 18% aq. NaCl solution washes were needed. The organic layer was polish filtered and the filter rinsed with MTBE (12.8 mL). It was then concentrated under reduced pressure to a minimum stirrable volume. The residual toluene in the residue was ≤10%. Ethyl acetate (60.8 mL) was added to the reaction mixture and the mixture was heated to no more than 50° C. to achieve a clear solution. The solution was cooled to 20-25° C., and n-heptane (86.3 mL) was added slowly with agitation. The suspension was stirred for at least 30 min at 20-25° C. and then stirred at least for 1 h at 0-5° C. The suspension was filtered and the cake was washed with 5:1 heptane/ethyl acetate (2×12.8 mL). The cake was dried under nitrogen and/or vacuum to provide the title compound, (1R,2S)-2-(((2,4-dimethylpyrimidin-5-yl)oxy)methyl)-2-(3-fluorophenyl)-N-(5-fluoropyridin-2-yl)cyclopropanecarboxamide, (14, 11.65 g) as a white to off white solid.

(1R,2S)-2-(((2,4-dimethylpyrimidin-5-yl)oxy)methyl)-2-(3-fluorophenyl)-N-(5-fluoropyridin-2-yl)cyclopropanecarboxamide: $^1$H NMR (500 MHz, DMSO-$d_6$) δ 11.19 (s, 1H), 8.31 (d, J=3.0 Hz, 1H), 8.12 (s, 1H), 7.94-7.85 (m, 1H), 7.62 (tt, J=8.7, 3.1 Hz, 1H), 7.44 (dd, J=10.6, 1.5 Hz, 1H), 7.41-7.40 (m, 1H), 7.39 (s, 1H), 7.14-7.06 (m, 1H), 4.67 (d, J 10.2 Hz, 1H), 4.29 (t, J=9.9 Hz, 1H), 2.63 (t, J=7.0 Hz, 1H), 2.38 (s, 3H), 2.03 (s, 3H), 1.76-1.64 (m, 1H), 1.49 (dd, J=8.0, 4.8 Hz, 1H); $^{13}$C NMR (125 MHz, DMSO-$d_6$) δ 168.68, 161.98 (d, $J_{CF}$=242.3 Hz), 158.46, 155.15, 155.38 (d, $J_{CF}$=247.9 Hz), 148.90, 148.51, 145.00 (d, $J_{CF}$ 7.7 Hz), 139.37, 135.15 (d, $J_{CF}$=24.9 Hz), 130.06 (d, $J_{CF}$=8.4 Hz), 125.05 (d, $J_{CF}$=19.5 Hz), 124.70 (d, $J_{CF}$=2.6 Hz), 115.71 (d, $J_{CF}$=21.7 Hz), 114.20 (d, $J_{CF}$=4.1 Hz), 113.70 (d, $J_{CF}$=20.9 Hz), 70.80, 34.09 (d, $J_{CF}$=1.9 Hz), 26.90, 24.38, 18.37, 17.78.

HRMS Calculated for $C_{22}H_{21}F_2N_4O_2$ [M+H]$^+$ 411.1627. found 411.1632.

H. Preparation of Compounds of Formula VI

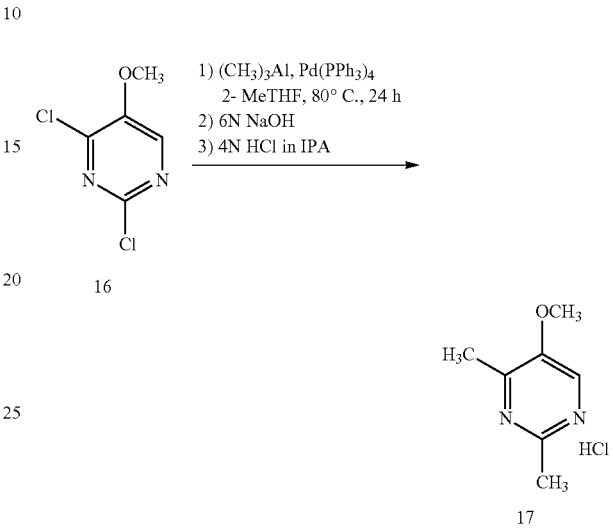

5-methoxy-2,6-dimethylpyrimidin-1-ium chloride (17)

2,4-Dichloro-5-methoxypyrimidine (16, 400 g, 2.23 mol, 1.0 equiv) was dissolved in 2-methyltetrahydrofuran (4.0 L). To this mixture was charged trimethylaluminum (2.0 M in heptane, 2200 mL, 2.0 equiv.), maintaining the internal temperature below 35° C. Tetrakis(triphenylphosphine)palladium(0) (25.8 g, 0.022 mol, 0.01 equiv.) was added and the mixture was heated to 80° C. The mixture was stirred for 24 h at 80° C., cooled to room temperature and added slowly to a cold (5-10° C.) aqueous sodium hydroxide solution (6 N, 4.0 L), maintaining the internal temperature of the quench solution below 15° C. (Caution: methane gas evolution). The mixture was warmed to room temperature and allowed to stir for 30 min after which stirring was halted and the phases allowed to split. The phases were separated. The upper organic phase was filtered through a pre-packed charcoal column (200 g) with aid of additional 2-methyltetrahydrofuran (1.0 L). The solution was concentrated to ⅔ volume. The mixture was diluted with fresh 2-methyltetrahydrofuran (4.0 L) and then concentrated under vacuum until 4.0 L of distillate had been collected. To the remaining solution was slowly added a solution of hydrogen chloride in isopropyl alcohol (5 M, 670 mL, 3.35 mol, 1.5 equiv.) resulting in the precipitation of a crystalline solid. The slurry was stirred for 1 h, and filtered. The wet cake was washed with 2-methyltetrahydrofuran (800 mL) and then dried under vacuum with a nitrogen sweep to afford 5-methoxy-2,6-dimethylpyrimidin-1-ium chloride (17, 279 g, 70% yield) as a pale yellow solid.

5-methoxy-2,6-dimethylpyrimidin-1-ium chloride: $^1$H NMR (500 MHz, DMSO-$d_6$) δ 8.60 (s, 1H), 3.97 (s, 3H), 2.68 (s, 3H), 2.49 (s, 3H); $^{13}$C NMR (126 MHz, DMSO-$d_6$) δ 160.14, 155.22, 150.35, 134.89, 57.02, 21.80, 18.46.

HRMS Calculated for $C_7H_{11}N_2O$ [M+H]$^+$ 139.0871. found 139.0874.

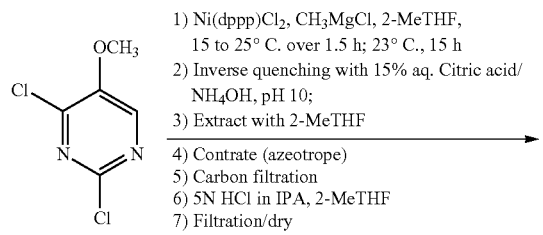

16

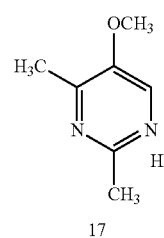

17

5-methoxy-2,6-dimethylpyrimidin-1-ium chloride (17)

A three-neck round bottom flask, fitted with a mechanical stirrer, an additional funnel, a temperature probe and $N_2$ inlet was charged sequentially with 2-MeTHF (330 mL, 10.5 vol, water content: <300 ppm), 2,4-dichloro-5-methoxy-pyrimidine (16, 30.0 g, 0.164 mol) (FWD Chem, Shanghai, China, or Amfinecom, Inc., St. Petersburg, Va.), and $NiCl_2$(dppp) (1.4 g, 2.6 mmol, 1.6 mol %). The resulting mixture was degassed by evacuation with a reduced pressure followed by purging with nitrogen gas (3 times at room temperature). The resulting mixture was cooled to 15° C. and a solution of 3 M Methyl magnesium chloride in THF (125 mL, 2.25 equiv.) was added via a dropping funnel maintaining the internal temperature at 15-25° C. over a period of 1.5 h (Note: first 6 mL of MeMgCl was added slowly at 15-20° C., and aged for 15 min to activate the catalyst). The dropping funnel was rinsed with 2-MeTHF (15 mL). After addition of the MeMgCl, the reaction was warmed to room temperature over 1 h with the aid of a cooling water-bath. The reaction was stirred for 13 h at room temperature with water-bath cooling (At this point, HPLC indicated the reaction was complete. Magnesium salt was precipitated as a golden yellow colored slurry). The resulting slurry was transferred into the pre-cooled (10° C.) 15% aqueous citric acid solution (300 mL) via cannula at such a rate to maintain the temperature below 30° C., and the biphasic mixture was vigorously stirred for 15 min. The reaction flask was rinsed with 2-MeTHF (60 mL). After stirring for 15 min, ammonium hydroxide (28%, 150 mL) was added keeping the temperature below 30° C. (the pH of the aq. Layer: ~10). The biphasic mixture was stirred for an additional 15 min. At this point, sodium chloride (83 g) was added and allowed to dissolve (=20 min) After phase separation, the aqueous layer was back-extracted with 2-MeTHF (300 mL). After a phase-cut, the organic layers were combined, concentrated and azeotropically dried (below 40° C.) by 2-MeTHF flush (300 mL). The precipitated inorganic salt was filtered through an in-line CUNO-filter, and rinsed with 120 mL of 2-MeTHF. The rinse was combined with the initial filtrate.

Salt Formation and Isolation:

The crude pyrimidine in 2-MeTHF (total volume 270 mL) was treated with 5 N HCl in 2-isopropanol (33 mL, 0.165 mol) at 10° C. The slurry was cooled to −10~−15° C. over 30 min, and aged for an additional 30 min at this temperature. The resulting slurry was filtered, and rinsed with pre-cooled 2-MeTHF (45 mL, −15° C.). The wet cake was dried under vacuum with a nitrogen sweep overnight to give 22.2 g (77.4%) of 2,4-dimethyl-5-methoxy-pyrimidine HCl salt, 17, as a yellow to orange colored crystalline solid, 5-methoxy-2,6-dimethylpyrimidin-1-ium chloride: $^1$H NMR (500 MHz, DMSO-d$_6$) δ 8.60 (s, 1H), 3.97 (s, 3H), 2.68 (s, 3H), 2.49 (s, 3H); $^{13}$C NMR (126 MHz, DMSO-d$_6$) δ 160.14, 155.22, 150.35, 134.89, 57.02, 21.80, 18.46.

HRMS Calculated for $C_7H_{11}N_2O$ [M+H]$^+$ 139.0871. found 139.0874.

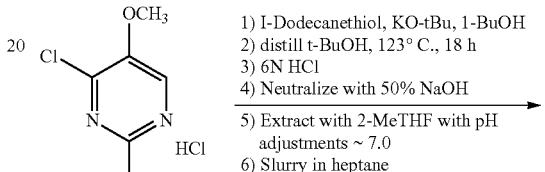

17

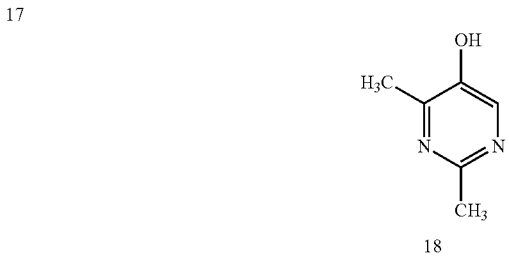

18

2,4-Dimethylpyrimidin-5-ol (18)

1-Butanol (158 mL) was added into the reaction flask which was fitted with a mechanical stirrer, a temperature probe, nitrogen inlet, and distillation equipment. The solvent was cooled to 10-15° C. and potassium t-butoxide (33.7 g, 0.3 mol) was charged in 3 portions maintaining an internal temperature less than 40° C. 1-Dodecanethiol (43.2 mL, 0.18 mol) was added to the resulting suspension, and was agitated at 20-25° C. for 30 min. 1-Dodecanethiol (43.2 mL, 0.18 mol) was added to the suspension and the mixture was stirred at room temperature for an additional 30 min. Next, 5-methoxy-2,6-dimethylpyrimidin-1-ium chloride, 17, (21 g, 0.12 mol) was added in 3 portions with efficient agitation, and the inlet was rinsed with 1-butanol (10 mL). The reaction flask was degassed with vacuum and purged with nitrogen (3×) and then maintained under a nitrogen atmosphere. The reaction mixture was heated to 117~120° C., and volatile tert-butanol (=30 mL) was collected. Then, the reaction was aged at reflux temperature (120-125° C.) for 20 h (conversion was 99.5%). The reaction mixture was cooled to 10-15° C., and 6 N HCl (90 mL) charged at 10-15° C. Deionized water was added (63 mL), and the reaction was aged for 20 min at room temperature. Heptane (126 mL) was added, agitated for 15 min, and allowed to split for 15 min. The product containing lower aqueous layer was drained to a suitable vessel. The upper organic layer was extracted with a combined solution of water (84 mL), 6 N HCl (21 mL) and MeOH (42 mL). The organic layer was back-extracted with water (42 mL). The aqueous layers were combined, and cooled to 10-15° C. The pH of the aqueous layer was adjusted to 6.8-7.2 with 50% sodium hydroxide (26 mL). Sodium chloride (37.8 g) was added, and the reaction was agitated for 30 min. 2-MeTHF (140 mL) was charged, agitated for 15 min, and allowed to split. The aqueous layer was back-extracted twice with 2-MeTHF (140 mL) with pH adjustment of the aqueous layer after each extraction (0.5 mL of 6 N HCl, desired pH in aqueous layer is 6.8~7.2). Note: The pH of the aqueous layer went up slightly after each extraction, and it should be adjusted accordingly (with 0.25 mL of 6 N HCl). The organic layers were combined and concentrated at reduced pressure to a minimum stirrable volume maintaining the internal temperature below 40° C. The concentrated solution was dried azeotropically with 2-MeTHF (3×65 mL), and then 2-MeTHF was charged to adjust the final solvent volume to 100 mL (any product on the wall of the reactor should be dissolved). Insoluble inorganic material was filtered off using a sintered glass funnel. The reactor and filter pot were rinsed with 2-MeTHF (40 mL). The filtrate was concentrated under a reduced pressure maintaining the internal temperature below 40° C. to ca. 60 mL of total batch volume. The reaction was next chased with heptane (4×80 mL) and the final batch volume was adjusted to a total volume of 65 mL. Then, the slurry mixture was cooled to 0-5° C. over 30 min, and aged for 1 h at this temperature. The resulting slurry was filtered, and the wet cake was rinsed with pre-cooled (0-5° C.) heptane (63 mL). The wet cake was dried under vacuum with a nitrogen flush at room temperature for 24 h to afford 11.6 g of 2,4-dimethylpyrimidin-5-ol, (18, 78~85% yield).

2,4-Dimethylpyrimidin-5-ol: $^1$H NMR (500 MHz, DMSO-$d_6$) δ 9.88 (s, 1H), 8.05 (s, 1H), 2.43 (s, 1H), 2.28 (s, 1H); $^{13}$C NMR (126 MHz, DMSO-$d_6$) δ 157.24, 153.71, 147.60, 141.80, 24.39, 18.33.

HRMS Calculated for $C_6H_9N_2O$ [M+H]$^+$ 125.0715. found 125.0720.

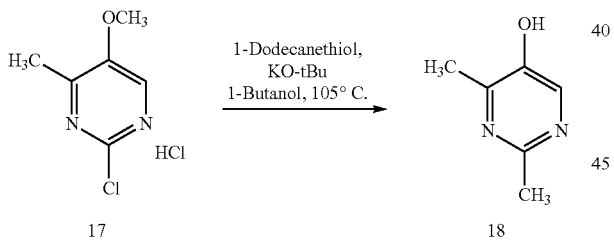

Alternate Preparation of 2,4-Dimethylpyrimidin-5-ol (18)

To a 22-Liter round bottomed flask was charged potassium tert-butoxide (1200 g, 11 mol, 3.5 equiv.) and 1-butanol (2700 mL). The mixture was stirred for 40 mins and then 1-decanethiol (1300 mL, 6.1 mol, 2.0 equiv.) was added. To the resulting slurry was added portionwise, 5-methoxy-2,6-dimethylpyrimidin-1-ium chloride (17, 532 g, 3.05 mol, 1.0 equiv.), using a minimal amount of 1-butanol for rinses as needed. The mixture was heated to 105-110° C. and stirred for 24 hours at this temperature. The mixture was cooled to room temperature and aqueous hydrochloric acid solution (6 N, 2000 mL) was added slowly, maintaining the internal temperature below 35° C. Heptane (2700 mL) was added and the mixture stirred for 10 mins. Stirring was halted and the phases were separated. The upper organic phase was backwashed with additional 6 N HCl solution (1000 mL). The aqueous phases were combined and neutralized by addition of aqueous sodium hydroxide solution (50% w/w, 789 mL) to pH=7-8, then extracted with 2-methyltetrahydrofuran (2×3000 mL) The 2-methyltetrahydrofuran was removed by vacuum distillation and replaced with heptane (3000 mL). The mixture was concentrated to near dryness and heptane (1300 mL was added). The resulting slurry was filtered and the wet cake was washed with heptane (3×400 mL). The cake was dried under vacuum with a nitrogen sweep to afford 2,4-dimethylpyrimidin-5-ol (18, 281 g, 74% yield) as an off-white solid.

2,4-Dimethylpyrimidin-5-ol: $^1$H NMR (500 MHz, DMSO-$d_6$) δ 9.88 (s, 1H), 8.05 (s, 1H), 2.43 (s, 3H), 2.28 (s, 3H); $^{13}$C NMR (126 MHz, DMSO-$d_6$) δ 157.24, 153.71, 147.60, 141.80, 24.39, 18.33.

HRMS Calculated for $C_6H_9N_2O$ [M+H]$^+$ 125.0715. found 125.0720.

That which is claimed is:

1. A process for making a compound of Formula IX:

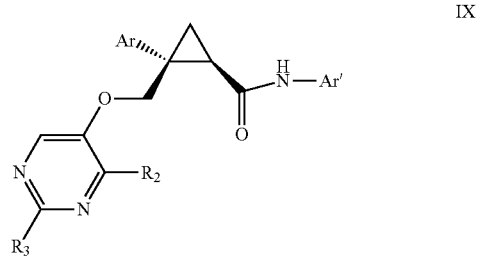

wherein:

Ar is phenyl, which phenyl may be unsubstituted, or substituted 1-3 times with substituents independently selected from the group consisting of: halo, $C_{1-6}$alkyl, $C_{1-6}$alkoxy, and halo$C_{1-6}$alkyl;

$R_2$ and $R_3$ are each independently selected from the group consisting of: hydrogen, $C_{1-6}$alkyl, halo$C_{1-6}$ alkyl, $C_{1-6}$alkoxy, and hydroxy$C_{1-6}$alkyl; and Ar' is a pyridine group:

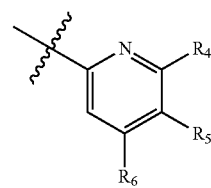

wherein:

$R_4$ is selected from the group consisting of: hydrogen, halo, $C_{1-6}$alkyl, $C_{1-6}$alkoxy, and ($C_{1-6}$alkoxy)$C_{1-6}$alkyl;

$R_5$ is selected from the group consisting of: hydrogen, halo, $C_{1-6}$alkyl, and halo$C_{1-6}$alkyl; and $R_6$ is selected from the group consisting of: hydrogen, halo, $C_{1-6}$alkyl, halo$C_{1-6}$alkyl, $C_{1-6}$alkoxy, ($C_{1-6}$alkoxy)$C_{1-6}$alkyl, and cyano, comprising the step of reacting a compound of Formula VII:

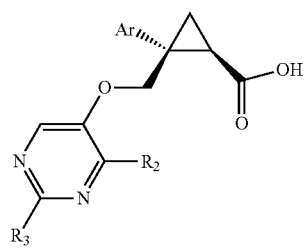

wherein Ar, $R_2$ and $R_3$ are as given above,
with a compound of Formula X:

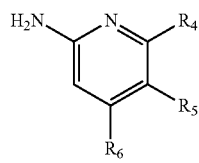

wherein $R_4$, $R_5$, and $R_6$ are as given above,
said reacting carried out in an organic solvent in the presence of an organic amine and an amide coupling agent,
to prepare said compound of Formula IX,
wherein said amide coupling agent is an alkyl phosphonic anhydride.

2. The process of claim 1, wherein Ar is unsubstituted or substituted 1-3 times with a halo independently selected from the group consisting of: chloro, fluoro, bromo, and iodo, and
$R_2$ and $R_3$ are each independently selected from the group consisting of: hydrogen and $C_{1-6}$alkyl.

3. The process of claim 1, wherein said organic solvent is selected from the group consisting of ethyl acetate, N,N-dimethylformamide (DMF), N,N-dimethylacetamide (DMA), N-methyl-2-pyrrolidone (NMP), acetone, toluene, acetonitrile, and dichloromethane.

4. The process of claim 1, wherein said amide coupling agent is a propyl phosphonic anhydride or tri-n-propyl phosphonic anhydride.

5. The process of claim 1, wherein said compound of Formula IX is:

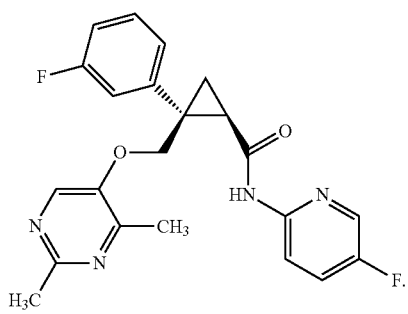 [SMILES: Cc1ncc(OC[C@@]2(c3cccc(F)c3)C[C@H]2C(=O)Nc2ccc(F)cn2)c(C)n1]

6. The process of claim 1, wherein said compound of Formula VII,

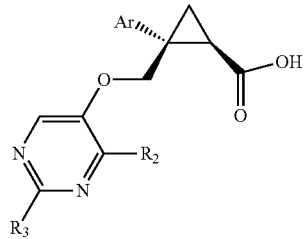

wherein Ar, $R_2$ and $R_3$ are as given in claim 1, is produced by a process comprising: oxidizing a compound of Formula V:

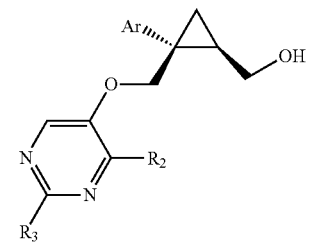

wherein Ar, $R_2$ and $R_3$ are as given above,
with sodium hypochlorite and sodium chlorite,
to thereby make said compound of Formula VII.

7. The process of claim 6, wherein said oxidizing with sodium hypochlorite and sodium chlorite is carried out simultaneously.

8. The process of claim 6, wherein said oxidizing is catalyzed with an effective amount of 2,2,6,6-tetramethylpiperidine 1-oxyl (TEMPO).

9. The process of claim 1, wherein said compound of Formula VII:

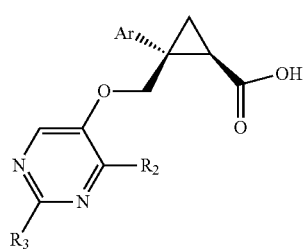

wherein Ar, $R_2$ and $R_3$ are as given in claim 1,
is produced by a process comprising the steps of:
a) oxidizing a compound of Formula V:

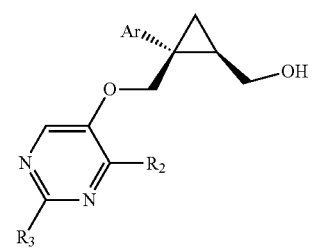

wherein Ar, $R_2$ and $R_3$ are as given above, with a first oxidizing agent, to form an aldehyde of Formula VIII:

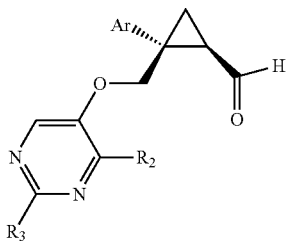

VIII wherein Ar, R$_2$ and R$_3$ are as given above; and then
b) oxidizing the aldehyde of Formula VIII with a second oxidizing agent,
to thereby make said compound of Formula VII.

10. The process of claim 9, wherein the first oxidizing agent is sodium hypochlorite.

11. The process of claim 9, wherein said oxidizing of step a) is catalyzed with an effective amount of 2,2,6,6-tetramethylpiperidine 1-oxyl (TEMPO).

12. The process of claim 9, wherein the second oxidizing agent is sodium chlorite.

13. The process of claim 6, wherein said compound of Formula V,

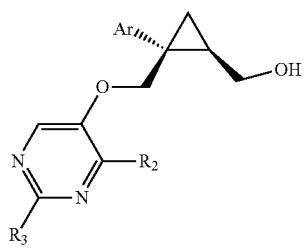

V wherein Ar, R$_2$ and R$_3$ are as given in claim 6, is produced by a process comprising the steps of:
a) stirring a mixture of:
i) a compound of Formula IV:

IV wherein Ar is as given above, and R$_1$ is a leaving group;
ii) a substituted pyrimidine of Formula VI:

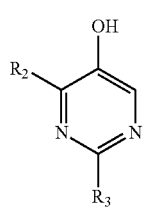

VI wherein R$_2$ and R$_3$ are as given above;
iii) a base; and
iv) an organic solvent, at a temperature of from 65-70° C., for 1 to 12 hours; and then
b) reacting the mixture with an aqueous base for a time of from 2 to 20 hours,
to thereby make said compound of Formula V.

14. The process of claim 13, wherein said compound of Formula IV:

IV wherein Ar is as given in claim 13, and R$_1$ is a sulfonate ester leaving group,
is produced by a process comprising reacting a compound of Formula III:

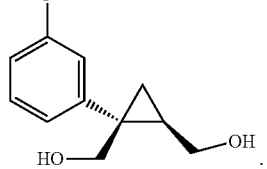

III wherein Ar is as given above,
with a compound selected from the group consisting of: tosyl chloride, mesyl chloride, nosyl chloride, toluenesulfonyl chloride, toluenesulfonic anhydride and methanesulfonic anhydride, wherein said reacting is carried out in an organic solvent in the presence of a base,
to thereby make said compound of Formula IV.

15. The process of claim 14, wherein the base is an organic amine or potassium carbonate.

16. The process of claim 14, wherein the organic solvent is selected from the group consisting of: dichloromethane, tetrahydrofuran, 2-methyltetrahydrofuran, toluene, acetonitrile, and ethyl acetate.

17. The process of claim 14, wherein said compound of Formula III is:

18. The process of claim 14, wherein said compound of Formula IV has the absolute stereochemistry of Formula IVa:

IVa wherein the compound has an enantiomeric excess (ee) of the Formula IVa stereoisomer of at least 80%.

19. The process of claim 14, wherein said compound of Formula IV is:

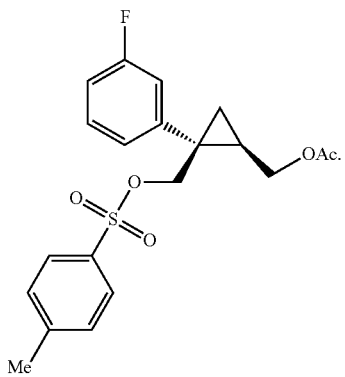 [SMILES: CC(=O)OC[C@@H]1C[C@@]1(COS(=O)(=O)c1ccc(C)cc1)c1cccc(F)c1]

20. The process of claim 14, wherein said compound of Formula III:

wherein Ar is as given in claim 14,
is produced by a process comprising reacting a mixture of:
i) a compound of Formula Ia:

wherein Ar is as given above;
ii) vinyl acetate;
iii) a lipase; and
iv) an organic solvent,
for a time of from 5 to 36 hours,
to thereby make the compound of Formula III.

21. The process of claim 20, wherein said lipase is a *Candida Antarctica* lipase.

22. The process of claim 20, wherein said compound of Formula III is:

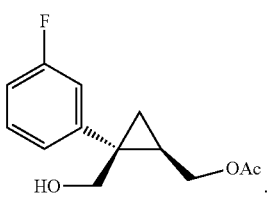 [SMILES: CC(=O)OC[C@@H]1C[C@@]1(CO)c1cccc(F)c1]

23. The process of claim 20, wherein a compound of Formula I:

wherein Ar is as given in claim 20,
is produced by a process comprising the steps of:
i) providing a composition comprising an organic solvent and a compound of Formula II:

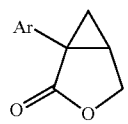

wherein Ar is as given above, and said composition is at a temperature of from −30 to 40° C.; and
ii) adding to said composition a hydride reducing agent which reduces said compound of Formula II into said compound of Formula I,
to thereby make said compound of Formula I which has the absolute stereochemistry of Formula Ia:

wherein Ar is as given above.

24. The process of claim 23, wherein Ar is unsubstituted or substituted 1-3 times with a halo independently selected from the group consisting of: chloro, fluoro, bromo, and iodo.

25. The process of claim 23, wherein the organic solvent is an aromatic hydrocarbon solvent, an aliphatic hydrocarbon solvent, a halogenated hydrocarbon solvent or an ether solvent.

26. The process of claim 23, wherein the hydride reducing agent is selected from the group consisting of: sodium borohydride, lithium borohydride, lithium aluminum hydride, lithium tributoxy aluminum hydride, diisobutylaluminum hydride, zinc borohydride, and lithium triethyl borohydride.

27. The process of claim 23, wherein the hydride reducing agent is lithium borohydride or lithium triethyl borohydride.

28. The process of claim 23, further comprising the step of quenching the reduction by adding to said composition a mild aqueous acid.

29. The process of claim 23, wherein the compound of Formula II has the absolute stereochemistry of Formula IIa:

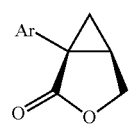

wherein Ar is as given in claim 23, and
the compound of Formula II has an enantiomeric excess (ee) of the Formula IIa stereoisomer of at least 80%.

30. The process of claim 23, wherein the compound of Formula II is the compound:
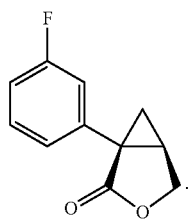 [SMILES: O=C1OC[C@@H]2C[C@]12c1cccc(F)c1]
31. The process of claim 23, wherein the compound of Formula I has an enantiomeric excess (ee) of the Formula Ia stereoisomer of at least 80%.
32. The process of claim 23, wherein the compound of Formula I is:
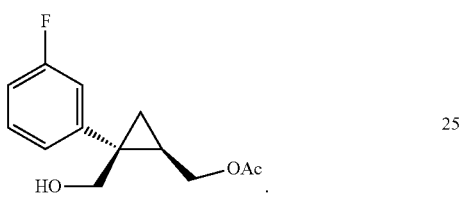
* * * * *